US011980766B2

(12) United States Patent
Woods et al.

(10) Patent No.: US 11,980,766 B2
(45) Date of Patent: May 14, 2024

(54) SHAPED INSULATING WASHER THAT PREVENTS MISALIGNMENT WHEN POSITIONED BETWEEN A FILTER CAPACITOR AND A FEEDTHROUGH

(71) Applicant: Greatbatch Ltd., Clarence, NY (US)

(72) Inventors: Jason Woods, Carson City, NV (US); Robert A. Stevenson, Canyon Country, CA (US); Christine A. Frysz, Orchard Park, NY (US); Thomas Marzano, East Amherst, NY (US); Keith W. Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 18/377,609

(22) Filed: Oct. 6, 2023

(65) Prior Publication Data

US 2024/0115868 A1    Apr. 11, 2024

Related U.S. Application Data

(63) Continuation-in-part of application No. 18/377,030, filed on Oct. 5, 2023.
(Continued)

(51) Int. Cl.
*A61N 1/05* (2006.01)
*A61N 1/375* (2006.01)

(52) U.S. Cl.
CPC .......... *A61N 1/3754* (2013.01); *A61N 1/05* (2013.01)

(58) Field of Classification Search
CPC ............ A61N 1/3754; A61N 1/3718; A61N 1/37512; A61N 1/375; A61N 1/05; A61N 1/08; A61N 1/372; H01G 4/35; H01G 4/236; H01G 4/224; H01G 4/30; H01G 4/40; H01G 4/38; H01G 2/103; H01G 2/106; H01G 4/228; H01G 5/00;
(Continued)

(56) References Cited

U.S. PATENT DOCUMENTS 3,137,808 A    6/1964  Coda et al.
5,489,180 A    2/1996  Ichihara et al.
(Continued)

FOREIGN PATENT DOCUMENTS

EP    3449973 A1    3/2019

*Primary Examiner* — Yingchuan Zhang
*Assistant Examiner* — Anh-Khoa N Dinh
(74) *Attorney, Agent, or Firm* — Michael F. Scalise

(57) ABSTRACT

A self-centering washer is positioned between the feedthrough and filter capacitor of a filtered feedthrough. The washer has openings through which first and second terminal pins extend. A first opening has an inner arcuate portion contacting the first terminal pin and an outer perimeter portion exposing the braze sealing the terminal pin to the insulator. A second opening has an inner arcuate portion contacting the second terminal pin and an outer perimeter portion exposing the braze sealing the terminal pin to the insulator. In an imaginary configuration with the first and second washer openings superimposed one on top of the other, the cumulative arcuate distance of the inner arcuate portions about one of the terminal pins, subtracting overlap, results in a gap between the superimposed washer openings that is less than a diameter of the first and second terminal pins so that the washer is prevented from lateral movement.

23 Claims, 13 Drawing Sheets

Related U.S. Application Data

(60) Provisional application No. 63/414,102, filed on Oct. 7, 2022.

(58) Field of Classification Search
CPC . H01G 5/01; H01G 5/011; H01G 2/12; H01G 2/14; H01G 4/005; H01G 4/012; H01G 4/018; H01G 4/12; H01G 2/00; H01G 4/00; H01G 7/00; H01G 9/00; H01G 11/00; H01G 13/00; H01G 15/00; H01G 17/00

See application file for complete search history.

(56) References Cited

U.S. PATENT DOCUMENTS

| | | |
|---|---|---|
| 6,882,248 B2 | 4/2005 | Stevenson et al. |
| 7,797,048 B2 | 9/2010 | Stevenson et al. |
| 7,878,747 B2 | 2/2011 | Dean et al. |
| 8,047,753 B2 | 11/2011 | Dean et al. |
| 9,064,640 B2 | 6/2015 | Brendel et al. |
| 9,447,810 B2 | 9/2016 | Dean et al. |
| 10,272,252 B2 | 4/2019 | Seitz et al. |
| RE48,348 E | 12/2020 | Stevenson |
| 11,344,734 B2 | 5/2022 | Stevenson et al. |
| 11,648,408 B2 | 5/2023 | Hussein |
| 11,764,745 B2 | 9/2023 | Sahabi et al. |
| 2009/0080140 A1* | 3/2009 | Iyer ................... B23K 35/0233 29/25.42 |

* cited by examiner

SHAPED INSULATING WASHER THAT PREVENTS MISALIGNMENT WHEN POSITIONED BETWEEN A FILTER CAPACITOR AND A FEEDTHROUGH

CROSS-REFERENCE TO RELATED APPLICATIONS

This application claims priority to U.S. provisional application Ser. No. 63/414,102, filed on Oct. 7, 2022.

This application is also a continuation-in-part of U.S. application Ser. No. 18/377,030, filed on Oct. 5, 2023.

FIELD OF THE INVENTION

The present invention generally relates to active implantable medical devices. More particularly, the present invention describes a self-centering washer that is positioned between the feedthrough and filter capacitor of a filtered feedthrough for an implantable medical device. The washer has at least first and second shaped openings through which first and second terminal pins extend. The first and second openings each have an inner arcuate or curved portion that contacts the respective terminal pin and an outer perimeter portion that exposes the respective braze sealing the terminal pin to the feedthrough insulator. In an imaginary configuration with the first and second washer openings superimposed one on top of the other, the cumulative arcuate distance measured in degrees of the inner arcuate portions about one of the terminal pins, subtracting overlap, results in a gap between the superimposed washer openings that is less than a diameter of the first and second terminal pins so that the washer is prevented from lateral movement along the planar face of the feedthrough insulator.

BACKGROUND OF THE INVENTION

The present invention relates to a filtered feedthrough assembly that is attachable to an active implantable medical device (AIMD). The filtered feedthrough assembly comprises a polymeric washer that is disposed between a feedthrough and a filter capacitor. The washer has openings through which terminal pins of the feedthrough extend. For example, with a feedthrough having first and second terminal pins, the washer has respective first and second openings. The first washer opening has a first inner arcuate or curved portion that contacts the first terminal pin and a first outer perimeter portion that is spaced from the first terminal pin and that exposes a portion of the first braze hermetically sealing the first terminal pin to the insulator in the first insulator via hole. Similarly, the second washer opening has a second inner arcuate or curved portion that contacts the second terminal pin and a second outer perimeter portion that is spaced from the second terminal pin and that exposes a portion of the second braze hermetically sealing the second terminal pin to the insulator in the second via hole.

Then, in an imaginary configuration having the first and second washer openings superimposed one on top of the other, the cumulative arcuate distance measured in degrees of the respective first and second inner arcuate portions about one of the first and second terminal pins, subtracting overlap, results in a gap between the superimposed first and second washer openings that is less than a diameter of either of the first and second terminal pins. That way, the polymeric insulating washer is prevented from any lateral movement with respect to a device side of the insulator.

Preferably, the first and second inner arcuate portions of the first and second openings each extend from about 90° to about 180° around the perimeter of the respective first and second terminal pins, and the first and second outer peripheral portions of the first and second openings each extend from about 90° to about 180° around the perimeter of the respective first and second brazes. Further, the opposed ends of the inner arcuate portions meet opposed ends of the outer peripheral portions at rounded corners.

Moreover, the terminal pins can be active terminal pins or ground terminal pins as, for example, in an internally grounded filter capacitor.

DETAILED DESCRIPTIONS OF THE PREFERRED EMBODIMENTS

Figure 1:
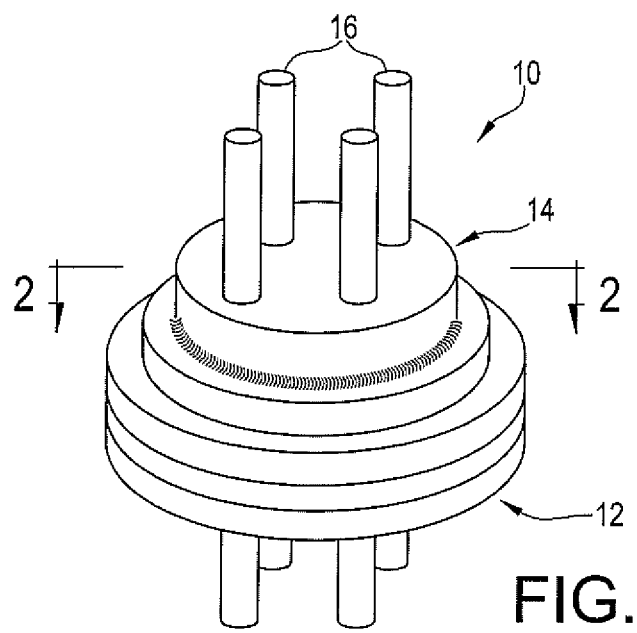
FIG. 1 illustrates a perspective view of a filtered feedthrough assembly 10 comprising a feedthrough 12 supporting a discoidal filter capacitor 14.
Figure 2:
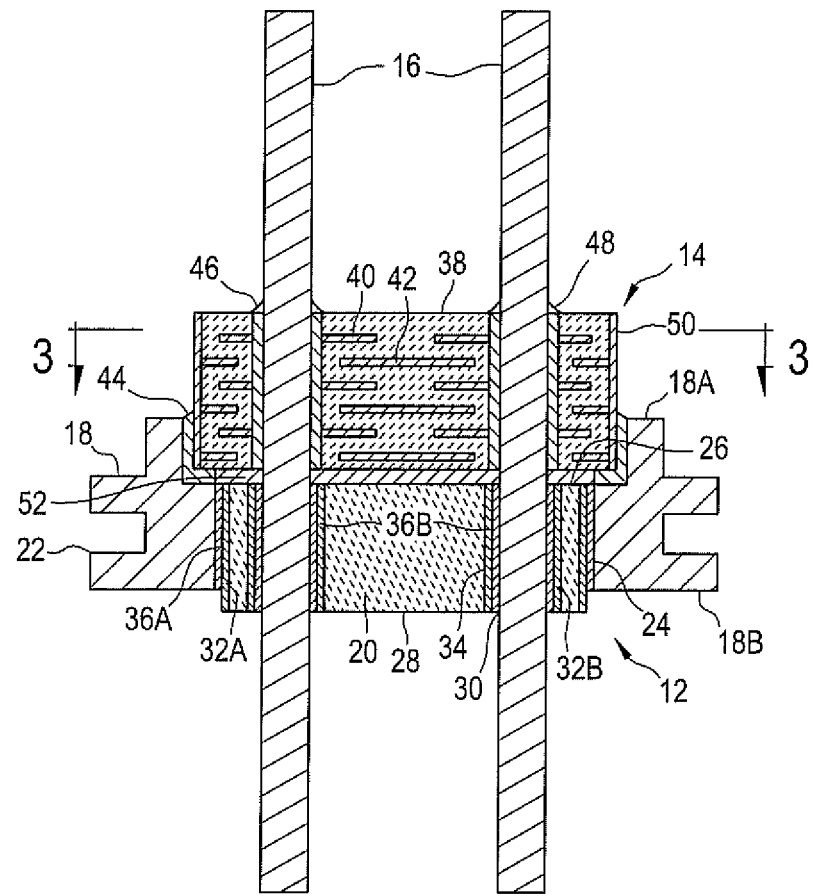
FIG. 2 shows a cross-sectional view of the filtered feedthrough assembly taken along line 2-2 of FIG. 1.
Figure 3:
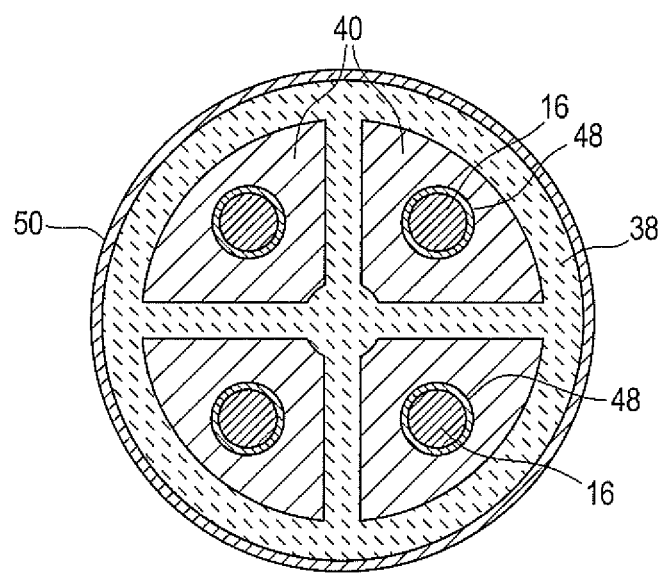
FIG. 3 illustrates a cross-sectional view of the filtered feedthrough assembly taken along line 3-3 of FIG. 2.

Referring now to the drawings, FIGS. 1 to 3 illustrate a filtered feedthrough assembly 10 comprising a feedthrough 12 supporting a discoidal filter capacitor 14. The filtered feedthrough assembly 10 is useful with medical devices, preferably implantable devices such as pacemakers, cardiac defibrillators, cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like.

The feedthrough 12 portion of the assembly 10 includes a plurality of terminal pins 16 that provide for coupling, transmitting, and receiving electrical signals to and from a patient's heart while hermetically sealing the interior of the medical device against ingress of body fluids that could otherwise disrupt device operation or cause device malfunction. While not necessary for accomplishing these functions, it is desirable to attach the filter capacitor 14 to the feedthrough 12 for suppressing or decoupling undesirable EMI signals and noise transmission into the interior of the medical device.

More particularly, the feedthrough 12 comprises a ferrule 18 defining an insulator-receiving opening formed by a ferrule sidewall extending from a ferrule first or device side 18A to a ferrule second or body fluid side 18B. The ferrule sidewall surrounds an insulator 20. Suitable electrically conductive materials for the ferrule 18 include titanium, tantalum, niobium, stainless steel, and combinations of alloys thereof, the former being preferred. The ferrule 18 may be of any geometry, non-limiting examples being round, rectangle, and oblong. A surrounding flange 22 extends from the ferrule 18 to facilitate attachment of the feedthrough 10 to the casing (not shown) of, for example, one of the previously described implantable medical devices. The method of attachment may be by laser welding or other suitable methods.

The insulator 20 is of a ceramic material such as of alumina, zirconia, zirconia toughened alumina, aluminum nitride, boron nitride, silicon carbide, glass, and combinations thereof. Preferably, the insulating material is alumina, which is highly purified aluminum oxide, and comprises a peripheral sidewall 24 extending to a first or device side 26 and a second or body fluid side 28. The insulator 20 is also provided with via holes 30 that receive terminal pins 16 passing therethrough.

An outer metallization 32A is applied to the insulator peripheral sidewall 24 while an inner metallization is applied to the insulator sidewalls 34 defining the terminal pin via holes 30. A first braze 36A hermetically seals between the ferrule 18 and the insulator peripheral sidewall 24. A second braze 36B hermetically seals between each of the terminal pins 16 and the insulator sidewalls 34 forming the terminal pin via holes extending through the insulator 20. Non-limiting examples of terminal pins 16 include platinum, platinum alloys, particularly platinum-iridium alloys, palladium, and palladium alloys. Non-limiting examples of braze materials include gold, gold alloys, and silver.

As further shown in FIGS. 1 to 3, the filtered feedthrough assembly 10 includes the filter capacitor 14 that provides for filtering undesirable EMI signals before they can enter the device housing via the terminal pins 16. The filter capacitor 14 comprises a ceramic-based dielectric substrate 38 having multiple opposite polarity electrode plates embedded therein. In the exemplary embodiment shown in FIGS. 1 to 3, the capacitor dielectric substrate 38 has a circular cross-section matching the cross-section of the ferrule 18 and supports a plurality of spaced-apart active electrode plates 40 that are interleaved with a plurality of spaced-apart ground electrode plates 42. The filter capacitor 14 is preferably joined to the feedthrough 12 adjacent to the insulator device side 26 by an annular bead 44 of conductive material, such as a conductive solder or braze ring, or a thermal-setting conductive adhesive, and the like.

The dielectric substrate 38 includes passageways 46 that are provided with an inner surface metallization layer. The terminal pins 16 pass through the passageways 46 and are conductively coupled to the active electrode plates 40 by an electrically conductive material 48 contacting between the terminal pins 16 and the inner metallizations. In a similar manner, the ground electrode plates 42 are electrically connected to the ferrule 18 through the conductive material 44 contacting an outer surface metallization 50 and the ferrule 18.

An insulating washer 52 is positioned between the feedthrough 12 and the filter capacitor 14. The insulating washer 52 fills in the air gap between the feedthrough 12 and the filter capacitor 14. Otherwise, the air gap could result in a high-voltage discharge or a catastrophic avalanche discharge between the positive and negative or active and ground poles of the filtered feedthrough assembly 10.

Figure 4:
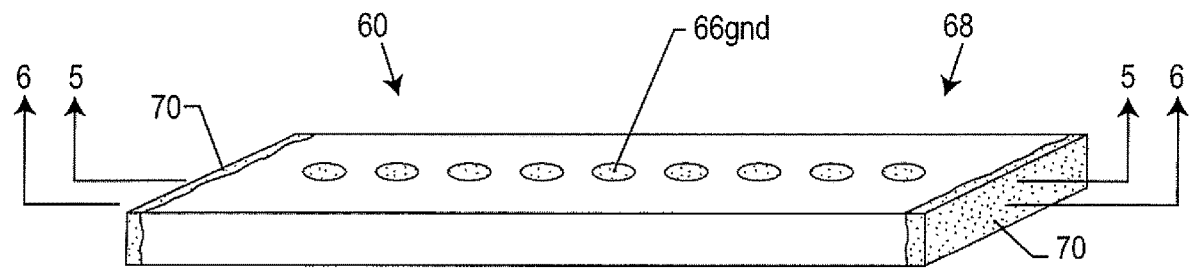
FIG. 4 is taken from FIG. 37 of U.S. Pat. No. 6,765,780 illustrating an isometric view of a hybrid rectangular feedthrough filter capacitor designed for both internal and external grounding.

FIG. 4 is an isometric view taken from FIG. 37 of U.S. Pat. No. 6,765,780 illustrating a hybrid internally grounded filter capacitor 60 designed for both internal and external grounding. The hybrid internally grounded filter capacitor design is best understood by referring to the cross-sectional view of FIG. 5.

Figure 5:
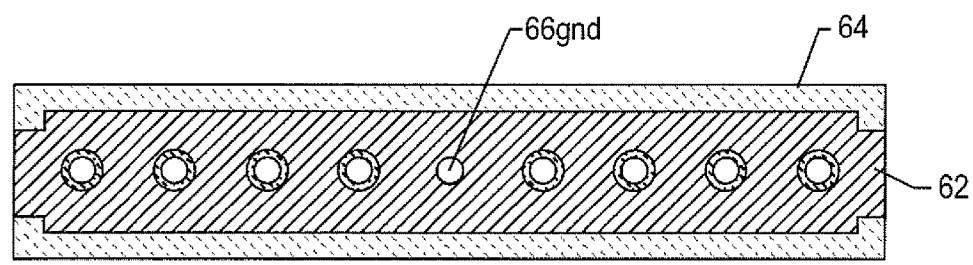
FIG. 5 is a cross-sectional view generally taken along section 5-5 of FIG. 4 illustrating a ground electrode plate.

FIG. 5 is generally taken along line 5-5 of FIG. 4 and illustrates a ground electrode plate 62 disposed on a ceramic substrate 64 with a central capacitor passageway for accepting a corresponding feedthrough centrally located ground terminal pin 66gnd. When the ground terminal pin 66gnd is electrically connected to the EMI filter capacitor 68, the feedthrough is then internally grounded.

FIG. 5 also illustrates that the ground electrode plate 62 selectively extends to both edges of the ceramic substrate 64. When the external edge ground metallizations 70 (shown at the left and right edges of the rectangular hybrid internally grounded filter capacitor 60 of FIG. 4) are electrically connected to a hermetically sealed feedthrough, the feedthrough is then externally grounded. Such internal and external grounding (i.e., electrical connections of an EMI filter capacitor passageway to a ferrule ground terminal and at least one selectively located external ground capacitor metallization 70 to a ferrule oxide-resistant pad, pocket-pad or braze hermetic seal) defines a hybrid internally grounded filter capacitor 60.

A hybrid internally grounded filter capacitor is a multi-point grounding system, which is important for ensuring that each active terminal pin 66 has a high degree of filter performance (high insertion loss performance that shows EMI attenuation at high frequencies). As such, long and narrow feedthrough filter capacitors must not solely be grounded internally by electrical connection to terminal pin 66gnd alone. The furthermost terminal pin from the internal grounded terminal pin 66gnd will likely exhibit highly degraded insertion loss performance due to parasitic inductance that builds up across the internal ground electrode plates 62.

In other words, by providing a multi-point grounding system, the hybrid internally grounded filter capacitor 60 is grounded internally at ground terminal pin 66gnd and at both external edge ground metallizations 70. In addition to the low inductance internal ground path, second and third low inductance edge ground paths are thereby provided. Accordingly, all of the terminal pins 66 of the hybrid internally grounded filter capacitor 60 will provide a high degree of filter performance.

Figure 6:
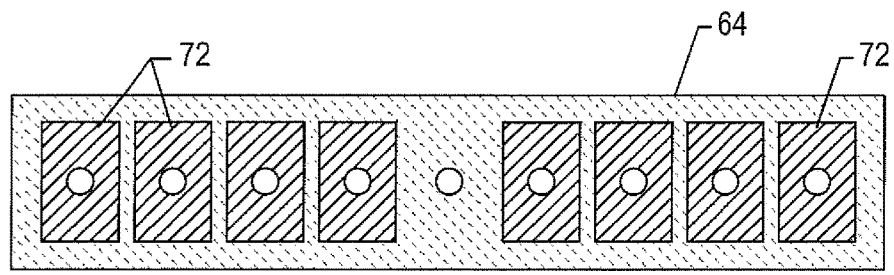
FIG. 6 is a cross-sectional view generally taken along section 6-6 of FIG. 4 illustrating eight active electrode plates on a single layer of a capacitor dielectric substrate.

FIG. 6 is a cross-sectional view generally taken along line 6-6 of FIG. 4. This drawing illustrates eight active electrode plates 72 disposed on a ceramic substrate 64. Each of the eight active electrode plates 72 is configured to receive a corresponding feedthrough terminal pin 66. The electrical connection material 65 disposed in the active conductive passageway of the EMI filter capacitor 60 electrically connects the filter capacitor's active conductive passageway metallization 67 to the feedthrough active terminal pin 111 hermetic seal gold braze 162.

Figure 7:
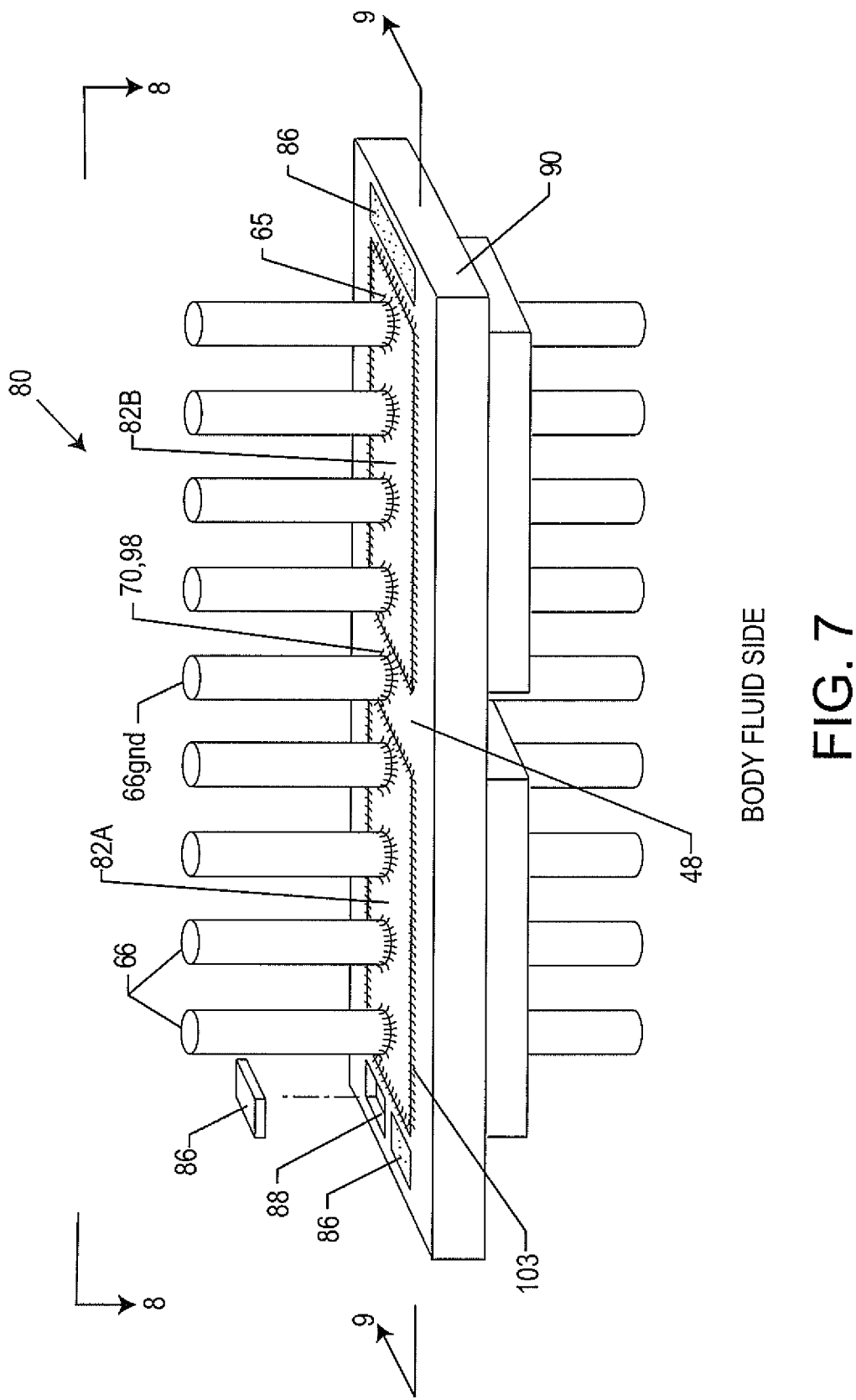
FIG. 7 illustrates an isometric view of a hybrid hermetically sealed feedthrough having two feedthrough insulators separated by a ferrule bridge.

FIG. 7 illustrates an isometric view of a hermetically sealed feedthrough 80 that is ready for electrical connection to the hybrid internally grounded filter capacitor 60 of FIG. 4. This embodiment has two feedthrough insulators 160A, 160B separated by a ferrule bridge 84. Also illustrated are gold braze pocket pads 86 within a ferrule pocket 88. The ferrule pocket 88 is a cavity with side walls, which fully contain the gold during the brazing process hermetically sealing the insulators 160A, 160B to the ferrule 90. The left side of FIG. 7 illustrates that the ferrule pocket 88 can be discontinuous (two unconnected pockets). It is understood that, while only two discontinuous pockets are shown, any number "n" of discontinuous pockets 88 may be present. On the right side, one continuous pocket 88 is shown. The one continuous pocket 88 can be any length or it can even extend about the perimeter of the ferrule 90. In addition to an electrical connection to the central ground terminal pin 66gnd, electrical connection of the ground external metallizations 70 of the hybrid internally grounded filter capacitor 60 of FIG. 4 can be made to the gold braze pocket pads 86, 88. Such a hybrid electrical connection ensures broadband high-frequency filter performance, as the hybrid electrical connection arrangement overcomes any performance issues associated with the previously disclosed parasitic inductances. In other words, all of the filtered feedthrough terminal pins 66 provide proper broadband high-frequency filter performance (reliably effective attenuation and insertion loss performance). FIG. 7 demonstrates that a ferrule bridge 84 comprising a ground terminal pin 66gnd is an alternative feedthrough ferrule design to a ferrule peninsula. Both ferrule structures provide effective internally grounding of an EMI filter capacitor.

Figure 8:
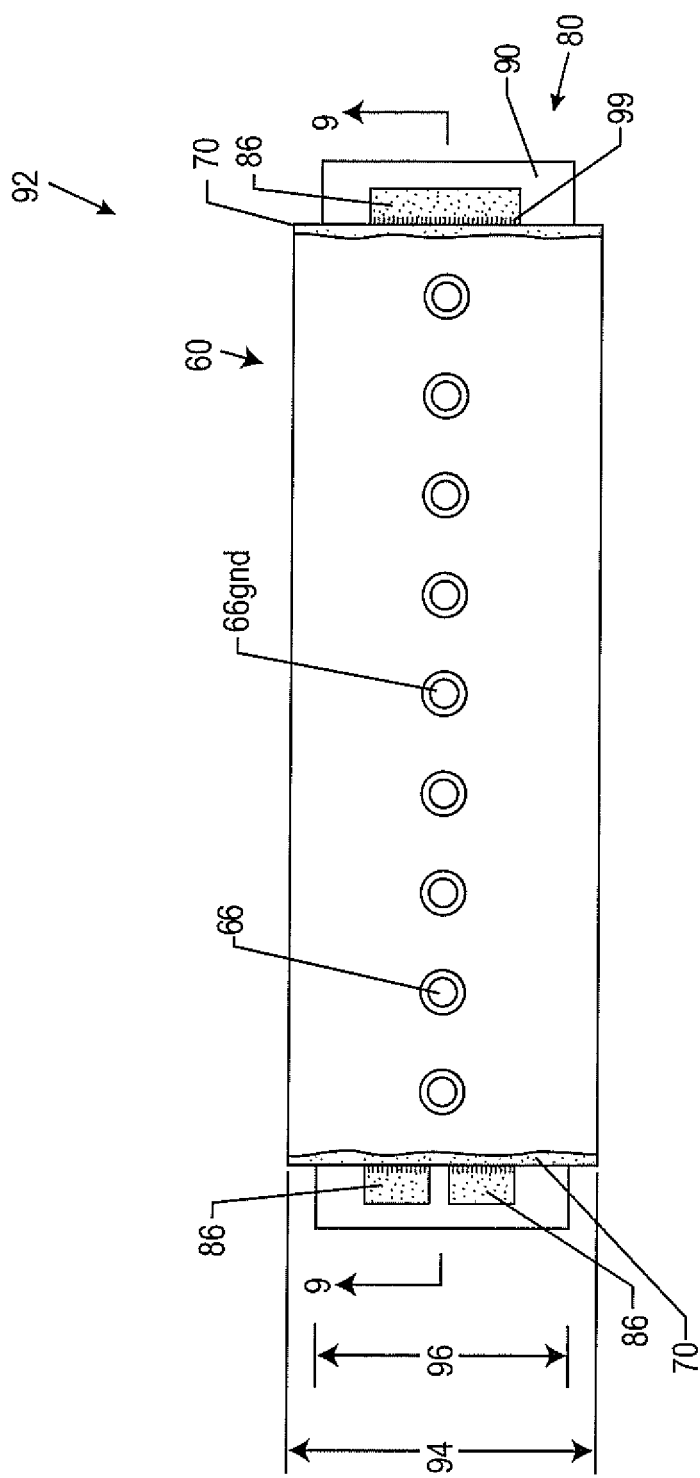
FIG. 8 illustrates a top view of the hybrid feedthrough filter capacitor of FIG. 4 mounted on the hermetically sealed feedthrough of FIG. 7.

FIG. 8 illustrates the hybrid internally grounded filter capacitor 60 of FIG. 4 mounted onto the hermetically sealed feedthrough 80 of FIG. 7 to form a filtered feedthrough 92. This embodiment shows that the rectangular hybrid internally grounded filter capacitor 60 has a width 94 greater than the ferrule width 96. As previously disclosed, an EMI filter capacitor having a width greater than that of the ferrule can greatly improve EMI filter volumetric efficiency. It is understood that the filtered feedthrough 80 of FIG. 8 can optionally comprise one or more telemetry terminal pins, which are not associated with the active electrode plates. A benefit of the embodiment of FIG. 8 is that the hybrid internally grounded filter capacitor 60 and the ferrule 90 have both been kept relatively long and narrow so that, even though the filter capacitor is wider than the ferrule, the filtered feedthrough will still fit into an AIMD without unduly increasing AIMD thickness. It is important that the AIMD be relatively thin so that it is comfortable for the patient after implant. It is understood that, while the terminal pin arrangement of FIG. 8 shows inline terminal pins, terminal pin arrangements may alternatively be staggered.

Figure 9:
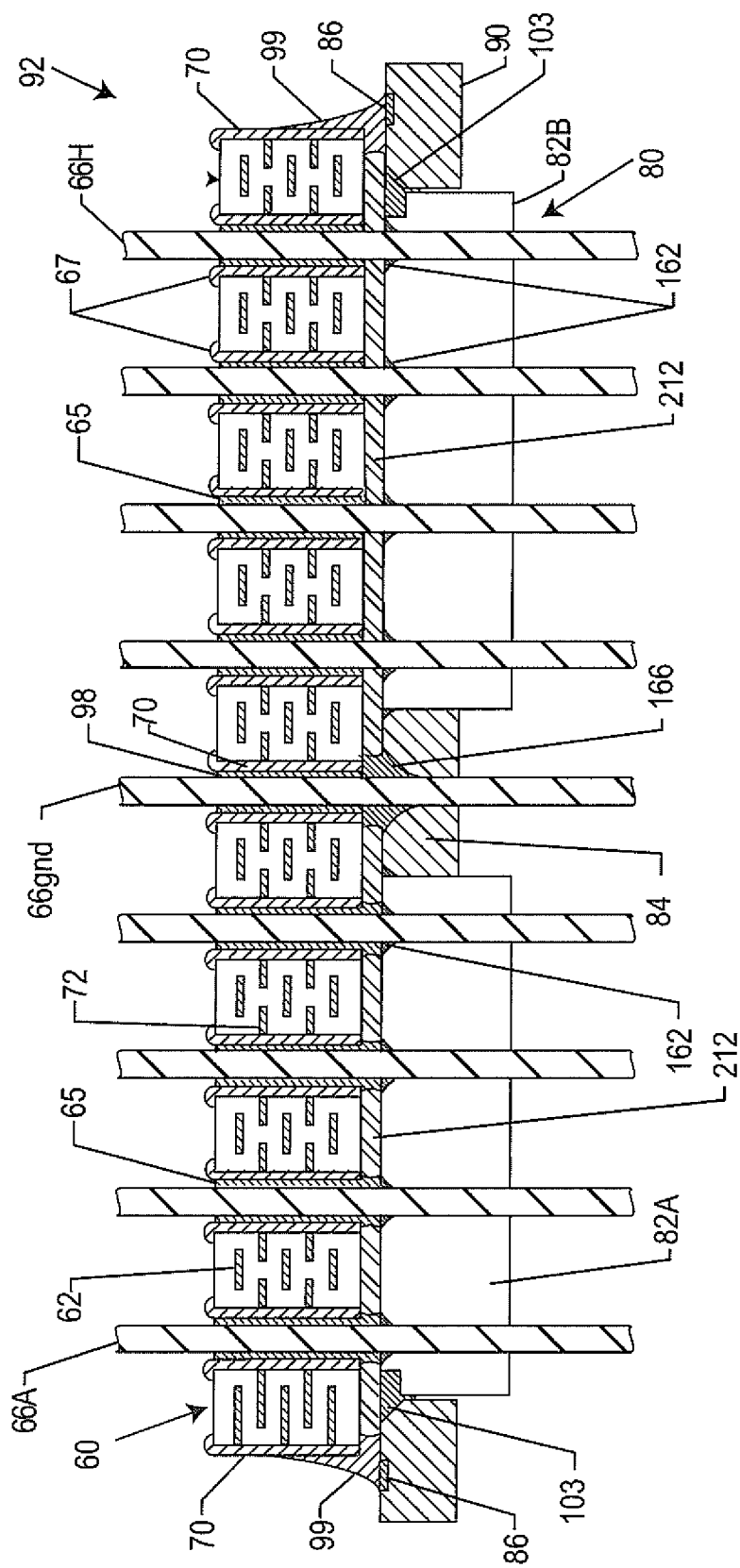
FIG. 9 is a cross-sectional view generally taken along section 38-38 of FIG. 8.

FIG. 9 is a cross-sectional view generally taken along line 9-9 of FIG. 8. The ground terminal pin 66gnd of the filtered feedthrough 80 is electrically connected to the passageway ground metallization 70 of the hybrid internally grounded filter capacitor 60 using electrical connection material 198. The external ground metallization 70 on the right and the left-hand sides of the hybrid internally grounded filter capacitor 60 is shown being electrically connected to gold braze pocket pads 86, 88 using electrical connection material 99. As previously disclosed, such a hybrid electrical ground connection ensures that the end terminal pins (66A, 66B, 66G and 66H) of the hermetically sealed feedthrough 80 are no longer relatively far from an electrical ground so that they will not exhibit substantial parasitic inductance. In other words, the multi-point electrical grounding of the hybrid internally grounded filter capacitor 60 can reliably provide significantly improved high-frequency filtering performance.

Figure 10:
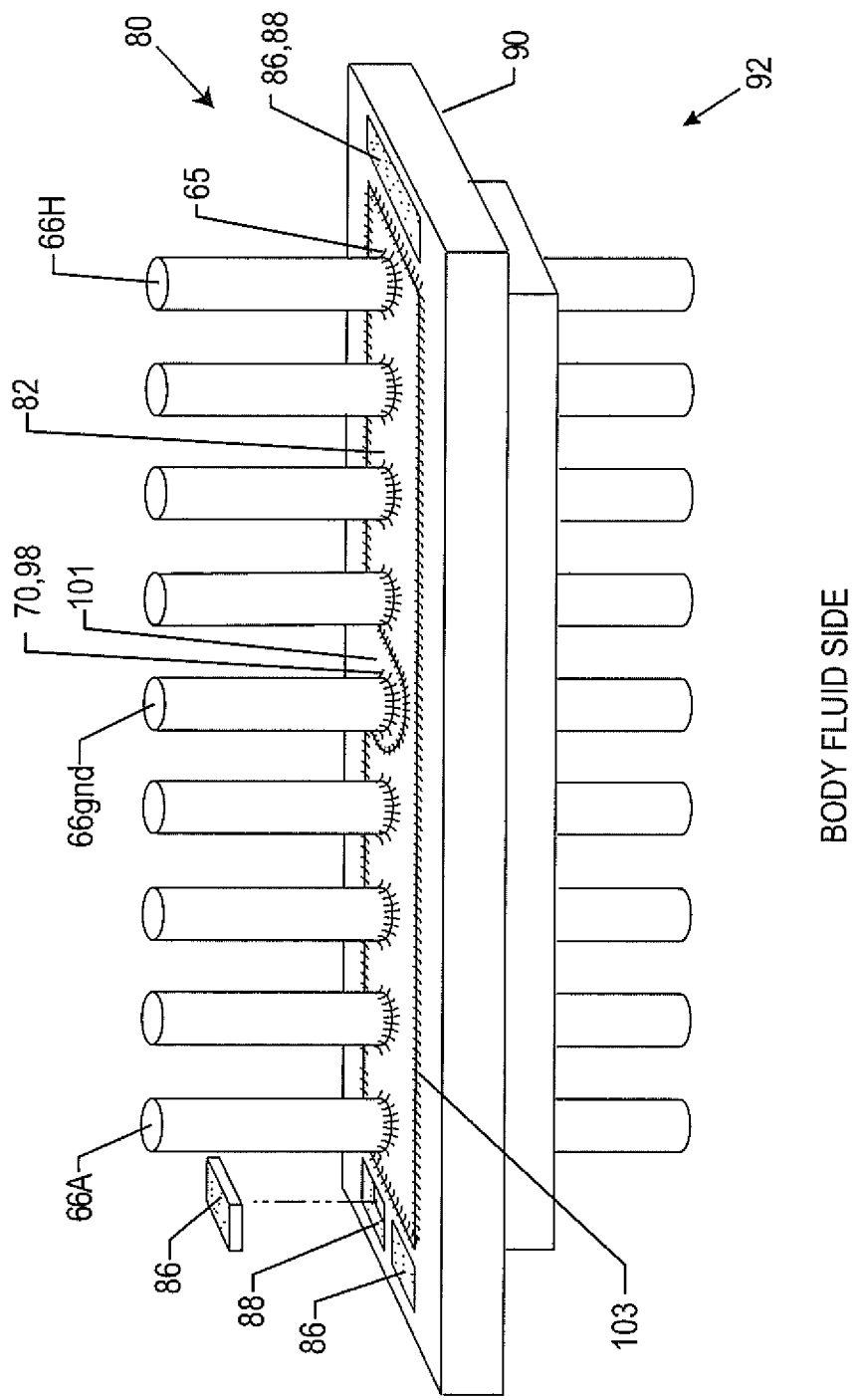
FIG. 10 is similar to FIG. 7, except that the central feedthrough ground terminal pin is electrically attached to a ferrule peninsula.

FIG. 10 illustrates a hermetically sealed feedthrough 80 having a ground terminal pin 66gnd mechanically and electrically connected to a ferrule peninsula 101. The ferrule peninsula 101 provides a feedthrough embodiment that has a single feedthrough insulator 82. In contrast, the ferrule bridge 84 of FIG. 7 provides a feedthrough embodiment that has two separate feedthrough insulators 82A and 82B. In either embodiment, the gold braze 103 hermetically seals each feedthrough insulator to the ferrule 90.

Figure 11:
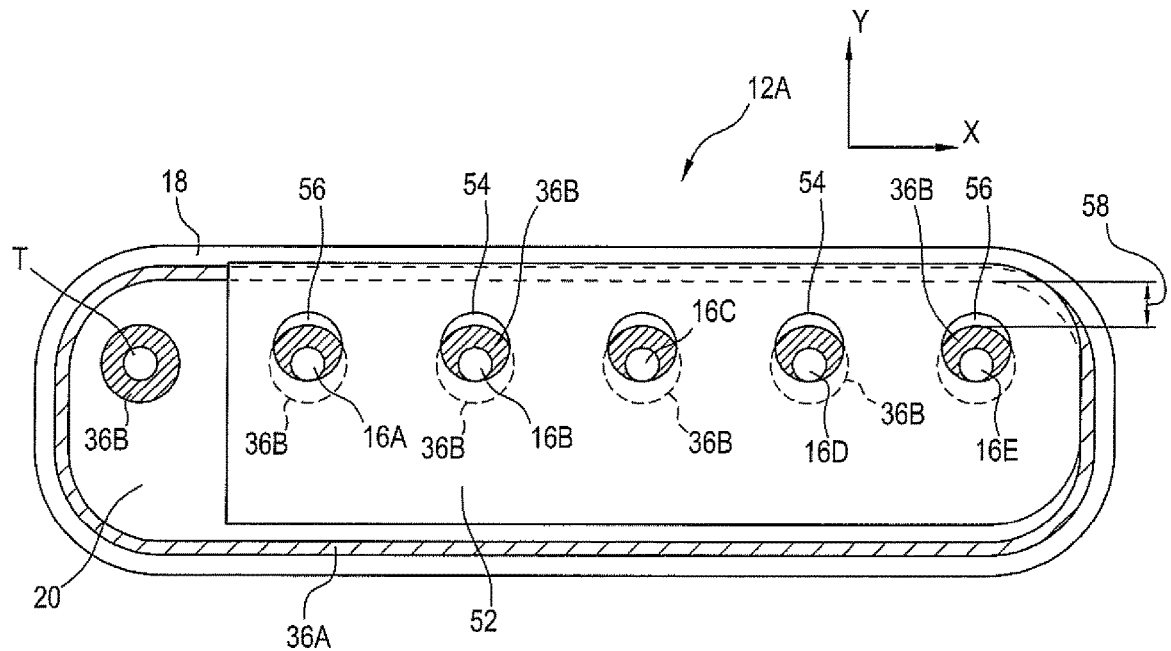
FIG. 11 is a plan view of a hermetically sealed feedthrough 12A similar to the feedthrough 12 shown in FIGS. 1 to 3 on which a prior art insulating washer 52 is undesirably misaligned over gold brazes 36B for terminal pins 16A to 16E, whose outside diameter is shown by hidden lines.

FIG. 11 is a plan view of another embodiment of a hermetically sealed feedthrough 12A that is useful in the above-described filtered feedthrough assembly 10. This drawing shows the prior art insulating washer 52 but with round-shaped openings 54 (which is typical) for receiving feedthrough terminal pins 16A to 16E. Because the insulating washer 52 has round-shaped openings 54, the washer can move about the terminal pins 16A to 16E into misaligned positions on top of the hermetically sealed feedthrough 12A. For example, using the x-y axis of FIG. 11 for directional referencing, the insulating washer 52 has undesirably moved upwardly along the y-axis. However, insulating washer 52 can also undesirably move downwardly along the y-axis, to the left along the x-axis, or to the right along the x-axis, and in a myriad of other undesirable misaligned positions.

In other words, the round-shaped openings 54 permit the washer 52 to misalign along the planar surface of the insulator 20 in any direction about the terminal pins 16A to 16E. The misalignment of washer 52 creates a gap 56 between the gold braze 36B and at least one of the active terminal pins 16A to 16E and the closest ground, which in this embodiment, is the ferrule gold braze 36A. The gap 56 can result in the highly undesirable effect of reducing the high-voltage keep-out zone 58, which is also the flashover distance. The gap 56 can be particularly problematic when the feedthrough 12A is exposed to a high volts per mil (V/mil) stress. Partial delamination can create an air bubble between the positive and negative or active and ground poles. Moreover, the gap 56 within the keep-out zone 58 of gold braze 36A can undesirably lead to a high-voltage discharge or a catastrophic avalanche discharge.

Commensurate with the amount of misalignment that exists, the misaligned insulating washer 52 will also undesirably cover a portion of the insulator-to-ferrule gold braze 36A. The covered portion of the gold braze 36A becomes unavailable for an oxide-resistant electrical connection.

It is noted that the telemetry pin T in the embodiment of FIG. 11 is not associated with a filter capacitor and is therefore not covered by the insulating washer 52. The reason the insulating washer 52 does not cover the telemetry pin T is that an AIMD telemetry pin is not filtered. Instead, the telemetry pin enables high-frequency RF communication between an external AIMD programmer and the implanted AIMD. This means that the telemetry pin T must not have any electrical connection to an EMI filter capacitor or an EMI filter circuit board. Otherwise, the RF telemetry signal would be undesirably attenuated. Moreover, a telemetry pin is either disposed in the header block, located outside the AIMD and is very small compared to an implanted lead, or is positioned in a separate area inside the AIMD. Accordingly, a telemetry pin does not tend to pick up much EMI and, therefore, does not need EMI filtering.

Insulating washers for use in filtered feedthrough assemblies are typically made from relatively lubricious polymeric materials. However, lubricious (slippery) thermoplastic coated polymeric insulating washers or homogeneous lubricious polymeric insulating washers are particularly problematic when it comes to centering their openings about terminal pins. Because a polymeric insulating washer must be applied and laminated to adjacent structures under significant pressure and high temperature, the washer can easily slide into a misaligned position covering at least a portion of the gold braze 36B hermetically sealing each of the terminal pins 16A to 16E to the sidewall 34 defining the respective terminal pin via holes 30 in the insulator 20.

Figure 12:
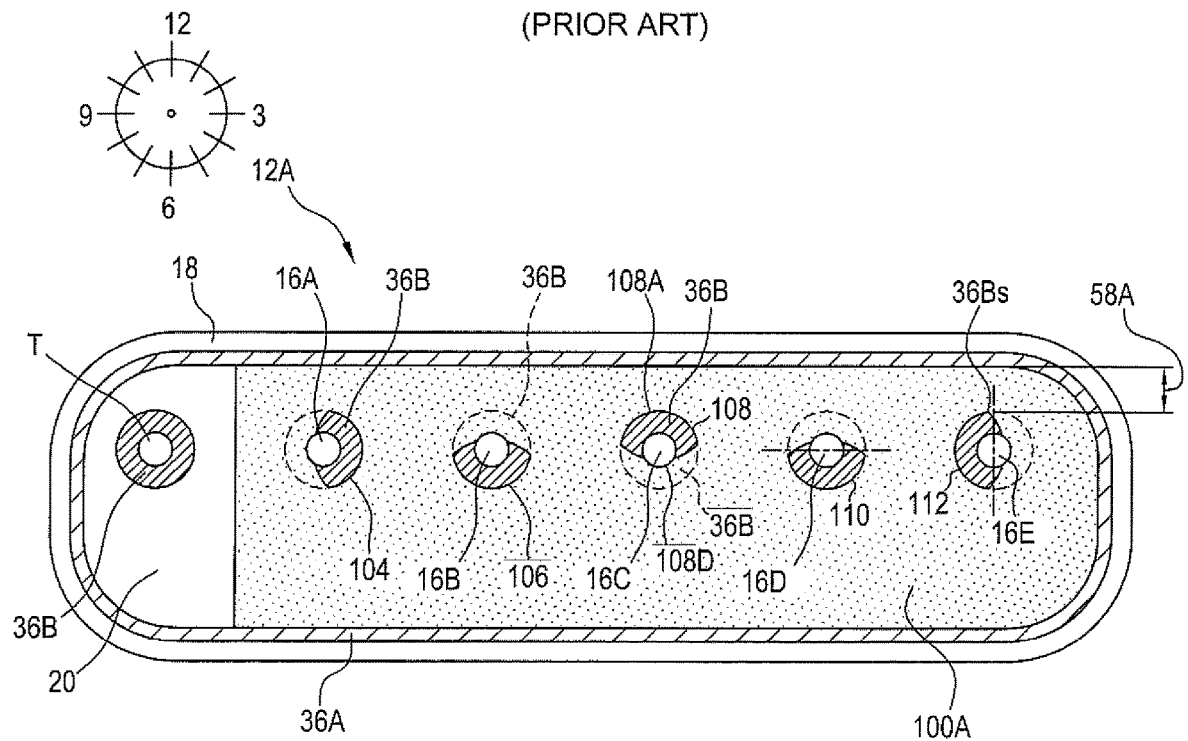
FIG. 12 is a plan view of a hermetically sealed feedthrough on which a self-centering insulating washer 100A according to the present invention is desirably located.

In that respect, FIGS. 12, 12A to 12D, 13 to 15 and 15A illustrate various embodiments for novel self-centering insulating washers 100A to 100E according to the present invention. In particular, FIG. 12 is a plan view of a hermetically sealed feedthrough 12A on which a novel self-centering insulating washer 100A is located about terminal pins 16A to 16E. The self-centering washer 100A has a number of novel baseball playing field-shaped openings 104 to 112 that receive a corresponding one of the terminal pins 16A to 16E.

Figure 12A:
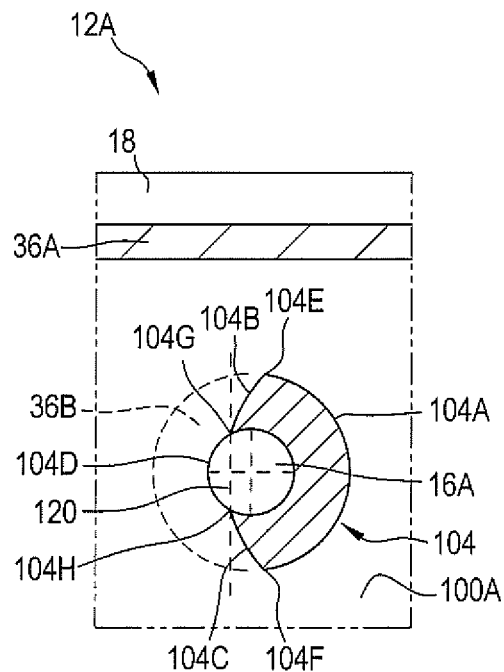
FIGS. 12A and 12B are sectional views of the insulating washer 100A shown in FIG. 5 self-centered about terminal pins 16A and 16B, respectively.

FIG. 12A focuses on baseball playing field-shaped opening 104 as an exemplary one of the openings 104 to 112. Opening 104 has an outer perimeter portion 104A that extends for about 90° to about 180° around the circular perimeter of the gold braze 36B which resides underneath the washer 100A at the terminal pin 16A. The outer perimeter portion 104A extends to opposed inwardly extending upper and lower edges 104B and 104C that in turn meet an inner arcuate portion 104D. The inner arcuate portion 104D faces the outer perimeter portion 104A and extends for about 90° to about 180° around the circular perimeter of the terminal pin 16A. The outer perimeter portion 104A meets the upper curved edge 104B at junction 104E and the lower curved edge 104C at junction 104F. Further, the upper curved edge 104B meets the inner arcuate portion 104D at junction 104G while the opposed lower curved edge 104C meets the inner arcuate portion 104D at junction 104H.

FIG. 12A also shows an imaginary x and y-axis coordinate system that is centered on the terminal pin 16A. An imaginary vertical line 120 extending through junctions 104G and 104H intersects the x-axis to the left of the y-axis. With this orientation of the shaped opening 104, the inner arcuate portion 104D is centered along the x-axis at about 9 o'clock with respect to the clock face shown in FIG. 12 and contacts the perimeter of the terminal pin 16A through an arc of about 90° to about 180°. This positioning means that only with respect to opening 104, the insulating washer 100A is capable of lateral movement only in a leftwards direction along the x-axis. Movement to the right along the x-axis is blocked by the inner arcuate portion 104D contacting the terminal pin 16A while movement in an upwardly direction and a downwardly direction along the y-axis is blocked by those portions of the inner arcuate portion 104D that reside immediate adjacent to the junctions 104G and 104H, respectively.

Figure 12B:
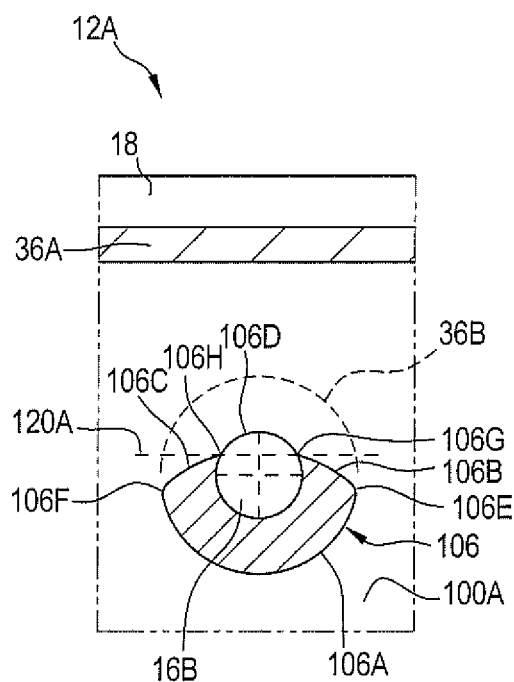

As particularly shown in FIG. 12B, opening 106 associated with terminal pin 16B has a shape that is similar to that of opening 104 about terminal pin 16A, except that its inner arcuate portion contacts the perimeter of the terminal pin 16B centered at about 12-o'clock with respect to the clock face shown in FIG. 12. Opening 106 has an outer perimeter portion 106A that extends from about 90° to about 180° about the circular perimeter of the gold braze 36B that resides underneath the washer 100A at terminal pin 16B. The outer perimeter portion 106A extends to opposed inwardly extending right and left edges 106B and 106C that in turn extend to an inner arcuate portion 106D. The outer perimeter portion 106A meets the right curved edge 106B at junction 106E and the left curved edge 106C at junction 106F. Further, the right curved edge 106B meets the inner arcuate portion 106D at junction 106G while the opposed left curved edge 106C meets the inner arcuate portion 106D at junction 106H.

FIG. 12B also shows an imaginary x-axis and y-axis coordinate system that is centered on the terminal pin 16B. An imaginary horizontal line 120A extending through junctions 106G and 106H intersects the y-axis above the y-axis. With this orientation of the shaped opening 106, the inner arcuate portion 106D is centered along the y-axis at about 12 o'clock with respect to the clock face shown in FIG. 12 and contacts the perimeter of the terminal pin 16B through an arc of about 90° to about 180°. This positioning means that only with respect to opening 106, the insulating washer 100A is capable of lateral movement in only an upwardly direction along the y-axis. Movement in a downwardly direction along the y-axis is blocked by the inner arcuate portion 106D contacting the terminal pin 16B while movement in a rightwards direction and a leftwards direction along the x-axis is blocked by those portions of the inner arcuate portion 106D that reside immediate adjacent to the junctions 106G and 106H, respectively.

Figure 12C:
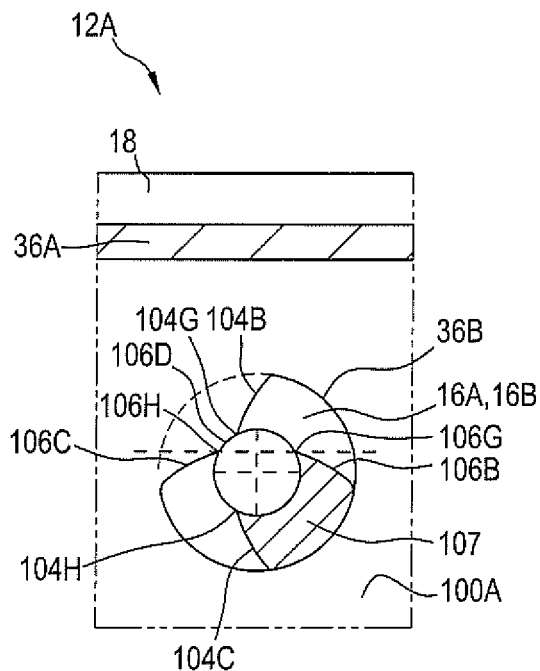
FIG. 12C shows openings 104 and 106 from FIGS. 12A and 12B superimposed on top of the other.
Figure 12D:
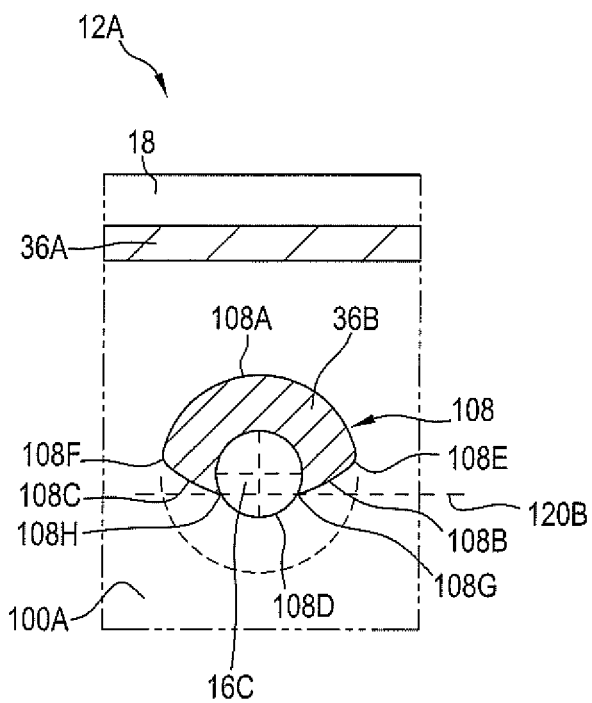
FIGS. 12D and 12E are sectional views of the insulating washer 100A shown in FIG. 5 self-centered about terminal pins 16C and 16E, respectively.
Figure 12E:
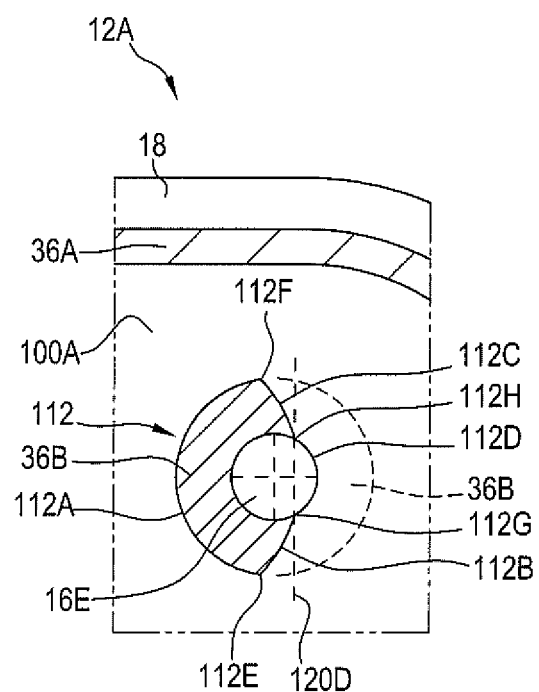

FIG. 12E shows that the opening 108 associated with terminal pin 16C has a shape that is similar to those of openings 104 and 106 about terminal pins 16A and 16B, except that its inner arcuate portion contacts the perimeter of the terminal pin 16C centered at about 6-o'clock with respect to the clock face shown in FIG. 12. Opening 108 has an outer perimeter portion 108A that extends from about 90° to about 180° about the circular perimeter of the gold braze 36B that resides underneath the washer 100A at terminal pin 16C. The outer perimeter portion 108A extends to opposed inwardly extending right and left edges 108B and 108C that in turn meet an inner arcuate portion 108D. The outer perimeter portion 108A meets the right curved edge 108B at junction 108E and the left curved edge 108C at junction 108F. Further, the right curved edge 108B meets the inner arcuate portion 108D at junction 108G while the opposed left curved edge 108C meets the inner arcuate portion 108D at junction 108H.

FIG. 12D also shows an imaginary x-axis and y-axis coordinate system that is centered on the terminal pin 16C. An imaginary horizontal line 120B extending through junctions 108G and 108H intersects the y-axis below the x-axis. With this orientation of the shaped opening 108, the inner arcuate portion 108d is centered along the y-axis at about 6 o'clock with respect to the clock face shown in FIG. 12 and contacts the perimeter of the terminal pin 16Bc through an arc of about 90° to about 180°. This positioning means that only with respect to opening 108, the insulating washer 100A is capable of movement only in a downwardly direction along the y-axis. Movement in an upwardly direction along the y-axis is blocked by the inner arcuate portion 108D contacting the terminal pin 16C while movement in a rightwards direction and a leftwards direction along the x-axis is blocked by those portions of the inner arcuate portion 108D that reside immediate adjacent to the junctions 108G and 108H, respectively.

Opening 110 has a similar structure and orientation as previously described for opening 106.

FIG. 12E shows that the opening 112 associated with terminal pin 16E has a shape that is similar to those of openings 104, 106, 108 and 110 about terminal pin 16A, 16B, 16C and 16D, respectively, except that its inner arcuate portion contacts the perimeter of the terminal pin 16E centered at about 3 o'clock with respect to the clock face shown in FIG. 12. Opening 112 has an outer perimeter portion 112A that extends from about 90° to about 180° about the circular perimeter of the gold braze 36B that resides underneath the washer 100A at terminal pin 16E. The outer perimeter portion 112A extends to opposed inwardly extending right and left edges 112B and 112C that in turn meet extend to an inner arcuate portion 112D. The outer perimeter portion 112A meets the right curved edge 112B at junction 112E and the left curved edge 112C at junction 112F. Further, the right curved edge 112B meets the inner arcuate portion 112D at junction 112G while the opposed left curved edge 112C meets the inner arcuate portion 112D at junction 112H.

FIG. 12E also shows an imaginary x-axis and y-axis coordinate system that is centered on the terminal pin 16E. An imaginary vertical line 120D extending through junctions 112G and 112H intersects the x-axis to the right of the y-axis. With this orientation of the shaped opening 112, the inner arcuate portion 112D is centered along the x-axis at about 3 o'clock with respect to the clock face shown in FIG. 12 and contacts the perimeter of the terminal pin 16E through an arc of about 90° to about 180°. This positioning means that only with respect to opening 112, the insulating washer 100A is capable of movement only in a rightwards direction along the x-axis. Movement in a leftwards direction along the x-axis is blocked by the inner arcuate portion 112D contacting the terminal pin 16E while movement in an upwards direction and a downwards direction along the y-axis is blocked by those portions of the inner arcuate portion 112D that reside immediate adjacent to the junctions 112G and 112H, respectively.

That way, with respect to an imaginary configuration where at least two of the shaped openings 104 to 112 are superimposed one on top of the other and with respect to their orientations in the washer, if the combined or cumulative arcuate distance measured in degrees of the respective inner arcuate portions 104D to 112D of the at least two shaped openings about a terminal pin, subtracting overlap, results in a gap between the combined inner arcuate portions of the superimposed openings that is less than the diameter of any one the terminal pins 16A to 16E (assuming equal diameters for the terminal pins 16A to 16F), then the novel self-centering insulating washer 100A illustrated in FIGS. 12, 12A, 12b, 12C and 12E is prevented from any lateral movement in a rightwards, leftwards, upwards, or downwards direction with respect to the feedthrough 12A.

For example, FIG. 12C shows openings 104 and 106, one superimposed on top of the other. The inner arcuate portion 104D of opening 104 extends from junction 104G to 104H. The inner arcuate portion 106D of opening 106 extends from junction 106G to junction 106H. As the drawings shows, the remaining portion 107 of one of the terminal pins 16A, 16B that is not contacted by one of the inner arcuate portions 104D and 106D extends from junction 104H of opening 104 to junction 106G of opening 106. A straight line intersecting those junctions 104H, 106G results in a gap that is less than the diameter of the terminal pins 16A and 16B. This means that the washer 100A is prevented from any lateral movement with respect to the device side 26 of the insulator 20.

If, on the other hand, with respect to an imaginary configuration with at least two of the shaped openings 104 to 112 being superimposed one on top of the other so that the combined or cumulative arcuate distance measured in degrees of the respective inner arcuate portions 104D to 112D about a terminal pin, subtracting overlap, results in a gap between the superimposed openings that is greater than the diameter of at least one of the terminal pins 16A to 16E (assuming equal diameters for the terminal pins 16A to 16E), then a third one of the shaped openings 104 to 112 is needed. That is with respect to an imaginary configuration where at least three of the shaped openings 104 to 112 are superimposed one on top of the other and with respect to their orientations in the washer so that the combined or cumulative arcuate distance measured in degrees of the respective inner arcuate portions 104D to 112D about a terminal pin, subtracting overlap, results in a gap between the superimposed openings that is less than the diameter of any one the terminal pins 16A to 16E (assuming equal diameters for the terminal pins 16A to 16F), then the novel self-centering insulating washer 100A illustrated in FIGS. 12, 12A, 12B, 12D and 12E is prevented from any lateral movement in a rightwards, leftwards, upwards, or downwards direction with respect to the feedthrough 12A.

Moreover, with respect to an imaginary configuration where there is no configuration with at least three of the shaped openings 104 to 112 being superimposed one on top of the other and with respect to their orientations in the washer so that the combined or cumulative arcuate distance measured in degrees of the respective inner arcuate portions 104D to 112D about a terminal pin, subtracting overlap, results in a gap between the superimposed openings that is greater than the diameter of at least one of the terminal pins 16A to 16E (assuming equal diameters for the terminal pins 16A to 16E), then a fourth one of the shaped openings 104 to 112 is needed. That is with respect to an imaginary configuration where at least four of the shaped openings 104 to 112 are superimposed one on top of the other and with respect to their orientations in the washer so that the combined or cumulative arcuate distance measured in degrees of the respective inner arcuate portions 104D to 112D about a terminal pin, subtracting overlap, results in a gap between the superimposed openings that is less than the diameter of any one the terminal pins 16A to 16E (assuming equal diameters for the terminal pins 16A to 16F), then the self-centering insulating washer 100A illustrated in FIGS. 12, 12A, 12B, 12D and 12E is prevented from any lateral movement in a rightwards, leftwards, upwards, or downwards direction with respect to the feedthrough 12A.

Thus, it is within the scope of the present invention that in order to prevent lateral movement of the self-centering insulating washer 100A in a rightwards, leftwards, upwards, or downwards direction with respect to the planar faces of the insulator and ferrule device sides of the feedthrough 12A, at least two of the shaped openings 104 to 112 are required. That is with respect to the shaped openings 104 to 112 being superimposed one on top of the other in an imaginary configuration so that the combined or cumulative arcuate distance measured in degrees of the respective inner arcuate portions 104D to 112D about a terminal pin, subtracting overlap, results in a gap between the superimposed openings that is less than the diameter of at least one of the terminal pins 16A to 16E (assuming equal diameters for the terminal pins 16A to 16E). That way, the novel insulating washer 100A of the present invention resolves the insulating washer mis-location or misalignment issues of the insulating washer embodiment illustrated in FIG. 11.

Referring once again to FIG. 12, the outer perimeter portions 104A, 106A, 108A, 110A and 112A of the shaped openings 104 to 112 for the washer 100A selectively expose the terminal pin-to-insulator gold brazes 36B at the respective terminal pins 16A to 16E so that the exposed braze portion resembles a baseball playing field with the terminal pin being analogous to home plate and the outer perimeter portion being analogous to the outfield home run fence bordering the braze 36B sealing the terminal pin to the insulator 20. The exposed gold brazes 36B allow for oxide-resistant electrical connections to an EMI filter capacitor or an EMI filter circuit board. Even though the gold brazes 36B, which hermetically seal the terminal pins 16A to 16E to the feedthrough insulator 20 are partially covered by the respective insulating washer openings 104 to 112, there is enough exposed gold for a low resistance, low impedance electrical connection.

In order for there to be a sufficient high-voltage stand-off distance, a keep-out zone 58A as the distance between the inner edge of the gold braze 36A of the insulator 20 to the ferrule 18 and the closest edge of one of the adjacent openings 104 to 112 is illustrated in FIG. 12. For example, the insulating washer-shaped opening orientation of the five pole in-line terminal pins 16A to 16E of FIG. 12 can be a challenge for providing sufficient stand-off distance. In high-voltage AIMDs, such as an ICD, or when low voltage AIMDs are exposed to defibrillation paddles or an automatic external defibrillator (AED), the high-voltage keep-out zone 58A becomes very important. It is a well-known principle in high-voltage engineering that any sharp point tends to be an equipotential field-line stress concentrator. In fact, a needle-point-shaped corner is actually one of the worst cases for high-voltage breakdown of air between conductors. In that respect, the sharper the corner, the greater the threat of dielectric breakdown.

For example, with reference to terminal pins 16A and 16E shown in FIG. 12, the respective opening 112 has an exposed gold braze 36B sharp point 36Bs that is oriented at about 12 o'clock and pointed directly into the high-voltage keep-out zone 58B. This is where a highest volts per mil (V/mil) stress may occur. On the other hand, the insulating washer shaped opening 108 about terminal pin 16C has its outer perimeter portion 108A having a relatively large radial contour. The large radial contour of the outer perimeter portion 108A faces the gold braze 36A, which is also at the edge of the high-voltage keep-out zone 58A. Comparing the sharp corner 36Bs of the insulating washer-shaped opening 112 about terminal pin 16E with the large radial contour 108A of the insulating washer-shaped opening 108 about terminal pin 16C, it is apparent that the latter design reduces the V/mil stress and is more unlikely to exhibit high-voltage breakdown than the sharp corner 36Bs at terminal pin 16E. Because the insulating washer opening 112 about terminal pin 16E exposes gold braze sharp corners 36Bs, the possibility of dielectric breakdown, which can lead to catastrophic high-voltage avalanche, is greater for the insulating washer openings 112 about terminal pin 16E than it is for the insulating washer opening 108 about terminal pin 16C. That is the case even though the exposed gold braze 36B of the terminal pins 16C and 16E have a keep-out zone 58A of the same distance.

Figure 13:
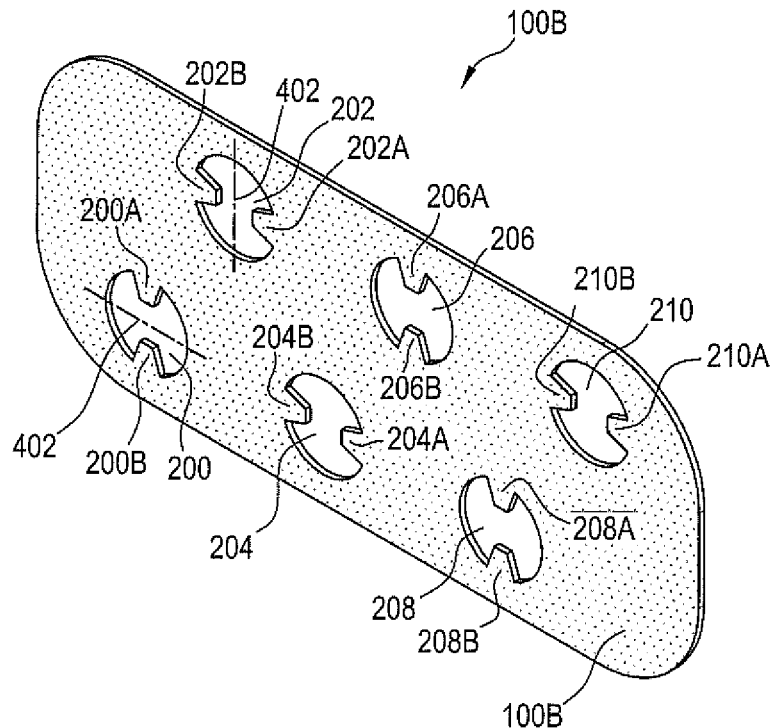
FIG. 13 is an isometric view of a novel self-centering insulating washer 100B that has shaped openings with two diametrically opposed inwardly extending tooth-like structures providing opposed inner arcuate portions.

FIG. 13 is an isometric view of another embodiment of a novel self-centering insulating washer 100B according to the present invention. The self-centering insulating washer 100B has uniquely shaped insulating washer shaped openings 200 to 210. Each opening has two diametrically opposed tooth-like structures or inwardly extending projections that provide opposed inner arcuate portions. In particular, opening 200 has opposed tooth-like projections 200A and 200B, opening 202 has tooth-like projections 202A, 202B, opening 204 has tooth-like projections 204A, 204B, opening 206 has tooth-like projections 206A, 206B, opening 208 has tooth-like projections 208A, 208B, and opening 210 has tooth-like projections 210A, 210B. The openings are oriented with an imaginary line centered between the tooth-like projections being oriented at 12 o'clock-6 o'clock (numerical designation 212) for openings 200, 204 and 208, and at 3 o'clock-9 o'clock (numerical designation 214) for openings 202, 206 and 210 in alternating pairs. When the insulator washer is seated on top of a hermetically sealed feedthrough, for example the feedthrough 12 shown in FIG. 2, the shaped openings 200 to 210 and their alternating orientations prevent inadvertent insulating washer movement in any lateral direction.

Moreover, it is within the scope of the present invention that the inner arcuate portions of the tooth-like projections of each of the openings 200 to 210 are configured to contact a terminal pin. Then, if both of the spaced apart gaps between the opposed inner arcuate portions contacting a terminal pin are less than the diameter of the terminal pin, the washer is prevented from any lateral movement with respect to the device side 26 of the insulator 20.

Figure 14:
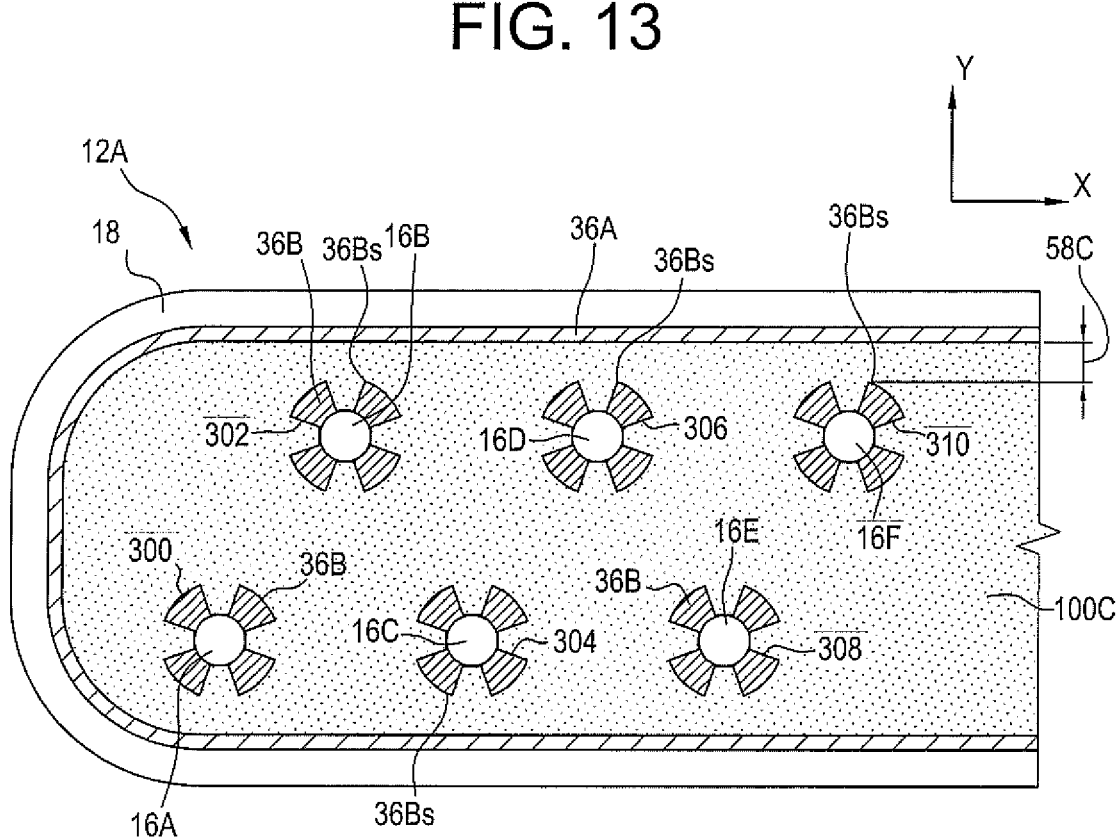
FIG. 14 is a plan view of a hermetically sealed feedthrough on which a novel self-centering insulating washer 100C having shaped openings with four inwardly extending tooth-like structures providing four inner arcuate portions.

FIG. 14 illustrates another embodiment of a self-centering insulating washer 100C disposed on a hermetically sealed feedthrough 12A. The self-centering insulating washer 100C is similar to the self-centering washer 100B of FIG. 13, except that each shaped opening 300 to 310 comprises four internal tooth-like structures (instead of two) that receive respective feedthrough terminal pins 16A to 16F. The four internal tooth-like structures provide four inner arcuate portions that properly align the self-centering insulating washer 100C about the terminal pins 16A to 16F. In that respect, the self-centering washer 100B does not require a unique orientation when mounted on the feedthrough 12. The four tooth-like structures for each opening, being symmetric, prevent inadvertent lateral misalignment. The four tooth-shaped openings 104 of the self-centering insulating washer 100C expose four portions of the gold braze 36B, each gold braze portion having exposed gold braze sharp corners 36Bs adjacent to the keep-out zone 58C. Those sharp corners 36Bs can be rounded (not shown) at the edge of the keep-out zone 58C to minimize electric field stress concentration, thereby increasing high-voltage breakdown strength. As previously disclosed, optimizing high-voltage keep-out area 58C is very important in preventing catastrophic electrical breakdown between the active terminal pins 16B, 16D, 16F, and the gold braze 36A and, in turn, the ferrule 18.

Figure 15:
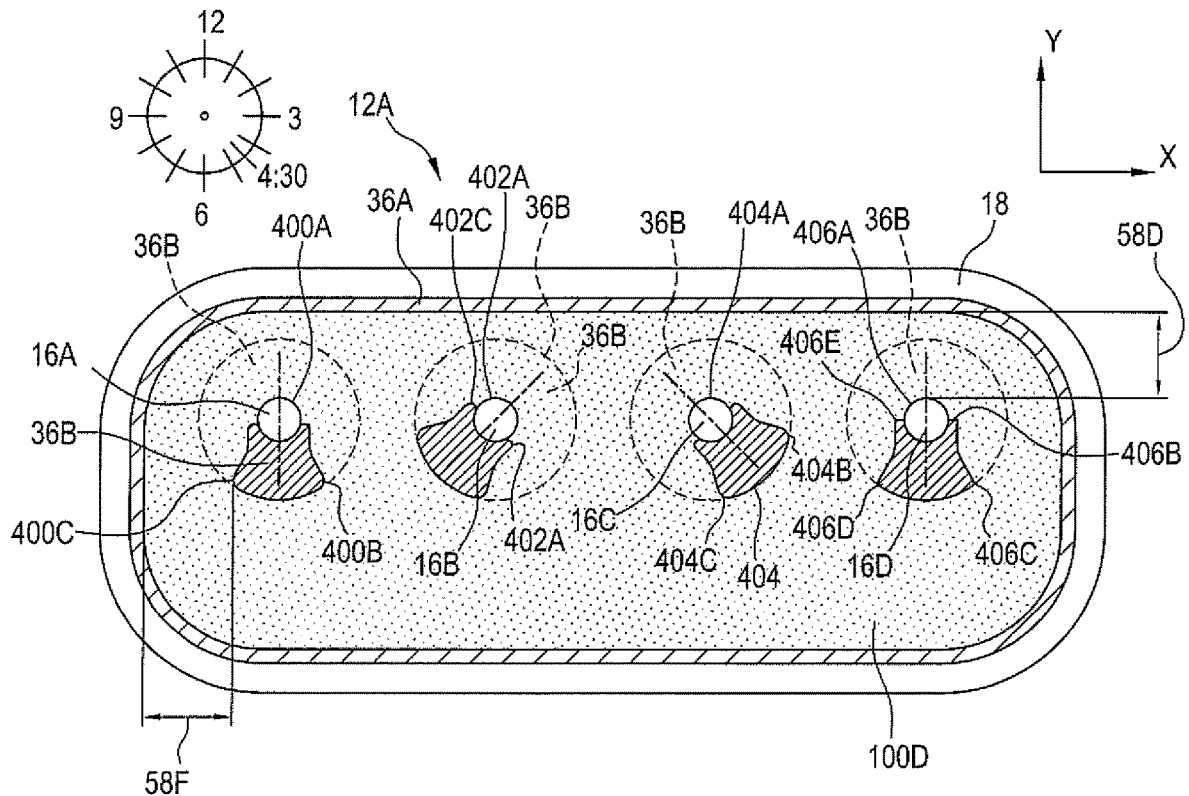
FIG. 15 is a plan view of a hermetically sealed feedthrough 12A on which a self-centering insulating washer 100D is desirably located so that the exposed insulator to terminal pin gold brazes 36B are outside of a high-voltage keep-out zone 58D.

FIG. 15 is a plan view of another embodiment of a washer having novel baseball playing field-shaped openings for a self-centering insulating washer 100D disposed on top of a hermetically sealed feedthrough 12A. In this embodiment, each baseball playing field-shaped opening 400, 402, 404 and 406 is oriented so that none of the exposed gold brazes 36B encroach into the increased distance keep-out zone 58D (i.e., none of these gold brazes 36B extend into the high-voltage keep-out zone 58D). In particular, the open portion of the gold braze adjacent to terminal pin 16A is generally oriented at 6 o'clock, the open portion of the gold braze adjacent to terminal pin 16B is oriented at 7:30 o'clock, the open portion of the gold braze adjacent to terminal pin 16C is oriented at 4:30 o'clock and the open portion of the gold braze adjacent to terminal pin 16D is oriented at 6 o'clock.

The increased keep-out zone 58D distance extends ideally to the external surface of each terminal pin 16A to 16D and to the insulator-to-ferrule gold braze 36A, thereby providing optimal high-voltage stand-off distance therebetween. Optimal high-voltage stand-off distance greatly improves insulative reliability by providing increased safety margins against high-voltage insults. Each insulating washer shaped opening 400 to 406 of the self-centering washer 100D has a baseball playing field-shaped opening that has a minor arc 400A, 402A, 404A and 406A abutting its corresponding terminal pin 16A to 16D. At least two insulating washer shaped openings must be selectively oriented to prevent the self-centering insulating washer 100D from undesirably moving in any lateral direction along the planar faces of the insulator and ferrule device sides of the feedthrough 12A. As previously disclosed, EMI filter capacitor or EMI filter circuit board electrical connection to the exposed gold brazes 36B is important in order to provide oxide-resistant low impedance, low resistance active terminal pin electrical connections.

Referring again to FIG. 15, on the left side, another high-voltage keep-out zone 58F is illustrated. This keep-out zone 58F extends to the rounded corner 400B of exposed gold braze 36B and to the insulator-to-ferrule gold braze 36A. As disclosed earlier, an exposed gold braze 36B at rounded corner 400B is preferred compared to the sharp corners 406B, 406C, 406D and 406E adjacent to terminal pin 16D.

Figure 15A:
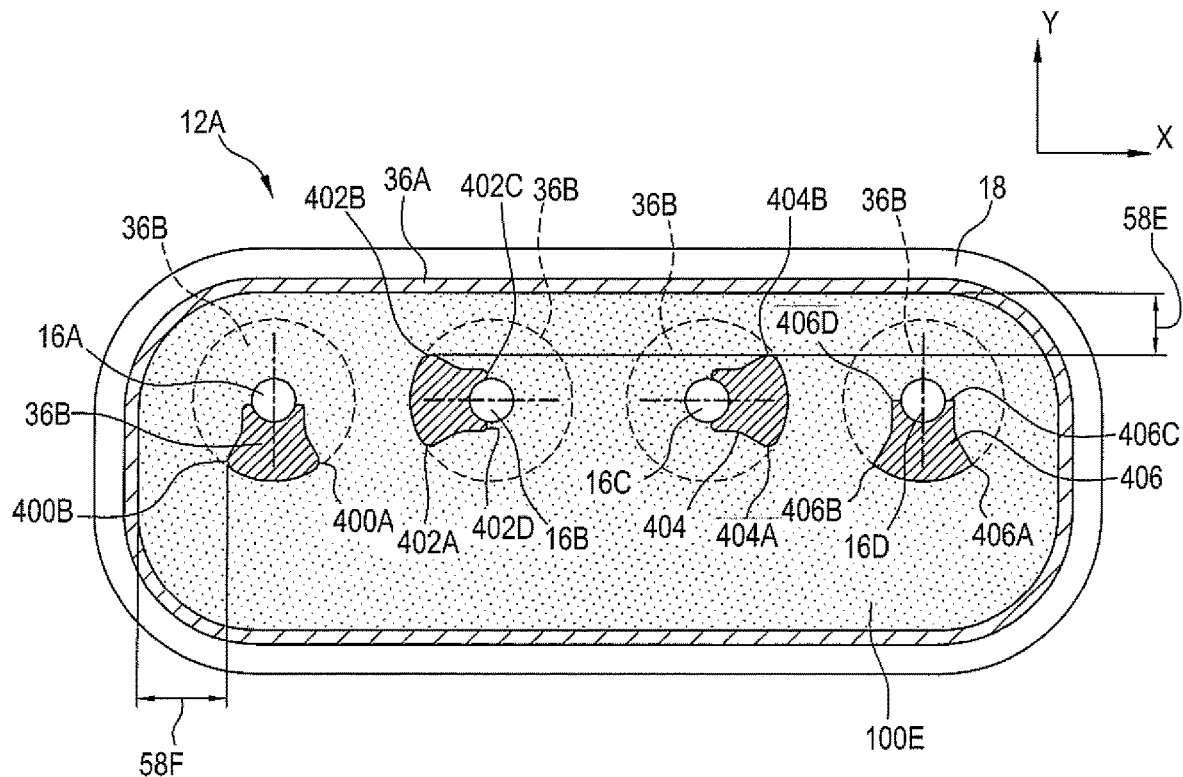
FIG. 15A is a plan view of a hermetically sealed feedthrough 12A on which a self-centering insulating washer 100E with terminal pins 16A to 16D received in baseball playing field-shaped openings for so that the exposed insulator to terminal pin gold brazes 36B are outside a narrower high-voltage keep-out zone 57E as compared to the embodiment shown in FIG. 15.

FIG. 15A is similar to FIG. 15, except that the open portion of the gold braze adjacent to terminal pin 16A is oriented at 6 o'clock, the open portion of the gold braze adjacent to terminal pin 16B is oriented at 9 o'clock, the open portion of the gold braze adjacent to terminal pin 16C is oriented at 3 o'clock, and the open portion of the gold braze adjacent to terminal pin 16D is oriented at 6 o'clock. As can be seen, the clocking-wise extent illustrated in this embodiment prevents inadvertent movement of insulating washer 100E in any lateral direction along the planar faces of the insulator and ferrule device sides of the feedthrough 12A.

The clock-wise orientations shown in FIG. 15A, however, position the exposed gold brazes 36B at a narrower keep-out zone 58E, as compared to the wider keep-out zone 58D of FIG. 15. The keep-out zone 58E shown in FIG. 8A, while reduced, is not reduced as much as, for example, the previous embodiments of FIGS. 12 and 15 (distance 58E is less than HV stand-off distance 58D). Corners 400A, 400B, 402A, 402B, 404A and 404B are radiused which helps reduce volts/mil stress.

Referring again to FIG. 15A, one also has to be concerned about the keep-out zone 58F, which has been previously discussed. In this case, keep-out zone 58F has a rounded corner 400B associated with active terminal pin 16A facing system ground gold braze 36A. The rounded corner as opposed to a sharp corner 406A, 406B, 406C and 406D is preferred. That is because the rounded corners have reduced volts/mil stress.

The self-centering washers 100A to 100E can be made using conventional punch and cut methods. Suitable materials for the washers 100A to 100E may be aromatic, semi-aromatic, aliphatic, partially fluorinated and combinations thereof, and include acrilates, epoxies, elastomers, phenolics, polyimides, polyolephins, and fluoropolymers. For example, suitable polymeric materials may be selected from silicone, polyurethane, polyester, polyethylene, polypropylene, polyamide (including synthetic polyamide, also known as nylon), acrylic, polyacrylates, and combinations thereof. Additional electrically insulative materials that are suitable for the washers 100A to 100E include flowable perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl copolymers including ethylene-vinyl acetate (EVA) or polyethylene-vinyl acetate (PEVA), polytetrafluoroethylene, ethylene tetrafluoroethylene, polyetherimide, acetal, polyacetal, polyformaldehyde, phenolic, polysulfide, and combinations thereof.

The materials for the washers 100A to 100E listed above may be used as a base for embedding and dispersing insulating nanoparticles, or one or more of the above-listed materials may be the insulating nanoparticles that are dispersed in another one of the above-listed insulating materials. The washers 100A to 100E may comprise layers, laminates, and coated structures or they may comprise composites of two different materials, such as a laminar composite structure comprising a core polymeric material and a surface polymeric material, a layered composite structure comprising one of: a laminar composite layer, an insulating nanoparticle-filled polymeric composite layer, a polymeric insulating layer, and combinations thereof. The washers 100A to 100E may be flexible, semi-rigid or rigid.

Suitable insulating nanoparticles are from $Al_2O_3$, BaO, CaO, $CeO_2$, MgO, $ZrO_2$, $SiO_2$, $TiO_2$, $Al_2SiO_{53}$, $BaTiO_3$, $SrTiO_2$, ZnO, $Si_3N_4$, zirconia toughened alumina (ZTA), alumina toughened zirconia (ATZ), yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof. The nanoparticles may be configured as particulates, short fibers, long fibers, spheres, flakes, submicron fibers, which are isotropically dispersed within the base polymeric material.

Methods for forming homogenously dispersed nanoparticle filled polymeric insulating washers 100A to 100E include sonication, ultrasonication, extrusion, three-roll milling, blowing, injection, in situ reactive blending, sol-gel processing, melt-mixing, thermo-kinetic (sheared) mixing, polymeric or pre-polymeric solution intercalation, in situ intercalative polymerization, melt intercalation, liquid crystal polymeric alloy formation, or nanofiller direct dispersion, among others.

In general, the smaller the nanoparticles, the higher the increase in insulator DBS (assuming a sufficient quantity and uniform distribution of the nanoparticles throughout the polymeric materials comprising the washers 100A to 100E and that the insulating material adequately wets the nanoparticles). Suitable nanoparticles sizes range from about 1 nm (0.001 µm) to about 40,000 nm (40 µm). In an embodiment, the nanoparticles range in size from about 1 nm (0.001 µm) to about 4000 nm (4 µm). In another embodiment, the nanoparticles range in size from about 1 nm (0.001 µm) to about 1000 nm (1 µm). The nanoparticles may further have at least one dimension that is less than or equal to 100 nm.

When the size of the nanoparticles decreases below about 100 nm, a markedly higher particle surface area-to-volume ratio is achieved compared with nanoparticle sizes above about 100 nm. Regarding a surface area-to-volume ratio, for the same particle loading, polymeric insulating materials having nanoparticle sizes that are less than or equal to about 100 nm have a much greater interfacial area than polymeric insulating materials filled with nanoparticles greater than about 100 nm in size. Higher interfacial area translates into higher dielectric breakdown strength. In contrast, nanoparticle filled polymeric insulating materials having particle sizes that are greater than about 100 nm have lower surface area-to-volume ratios, therefore lower interfacial area and, in turn, lower dielectric breakdown strength. In an embodiment, a nanoparticle filled polymeric insulating material comprises a particle size less than or equal to about 100 nm.

Depending on the size and morphology of the nanoparticles, nanoparticle loadings can range from >0% to ≤90%, by weight. Related to particle size is the particle surface area, which increases with decreasing particle size. In various embodiments, the loading of nanoparticles having particle sizes ranging from about 1 nm to <1000 nm is >0 to about 40%, by weight, in any one of the polymeric insulating washers 100A to 100E. In a further embodiment, the nanoparticle loading of a nanoparticle filled polymeric insulating washer 100A to 100E having particle sizes ranging from about 1000 nm to about 40,000 nm is >40% to ≤90%, by weight.

An alternative to a nanoparticle-filled polymeric insulating washer is an insulating nanolaminate polymeric insulating washer having layers of high dielectric constant nanomaterials interlayered with polymeric insulating layers. High dielectric constant nanolaminate layers are fully dense, ultra-fine-grained solids that exhibit a relatively high concentration of interfacial defects, which encourage adhesion to the interlayered polymeric insulating layers. Multilayer nanolaminates comprising interlayering of high dielectric constant and polymeric insulating layers can be grown using atom-by-atom deposition techniques that are designed with different stacking sequences and layer thicknesses. The properties of such fabricated nanolaminates depend on their compositions and thicknesses. These can be demonstrated within the synthesis process by thickness control of each layer and interfacial chemical reaction between layers. Multilayer laminates exhibit high strength efficient dielectric constants with high insulation characteristics. The electrical properties of such laminates may further be modified by incorporating dopants and site-engineering techniques, as well as layer-by-layer structure order and arrangement, which can both be suitable for improving insulative or dielectric properties of the nanolaminates.

Insulating nanoparticle fillers enhance various polymeric insulating material electrical and thermal properties, like increasing dielectric breakdown strength (DBS) and maximizing the dielectric breakdown field (EBD). Other material property enhancements include minimizing electric current leakage, increasing high-temperature electrical insulation breakdown, improving thermal conductivity, advantageously adjusting the coefficient of the thermal expansion, managing elasticity and/or flexibility, and boosting the mechanical and/or thermal endurance of the composite (hybrid) polymeric insulating material.

The primary advantage of insulating nanoparticles is their small size, which provides a large nanoparticle surface area, which, in turn, imparts to the nanoparticle filled polymeric insulating material a large interfacial area per unit volume. The large interfacial area per unit volume of the nanoparticle filled polymeric insulating material can thereby afford advantageous dielectric response and breakdown strength. The insulating nanoparticles may have various morphologies, including spherical, fiber-like, irregular, or custom shapes, or they can be thin, flattened, elongated in shape, where, for example, there is dimensional prominence in one particular dimension similar to a disk, a flake, or potato chip-like shape, or an essentially nano-sized two-dimensional sheet-like shape. The filler nanoparticles may all be of the same size or, alternatively, may comprise a blend of different nanoparticle sizes and/or shapes.

It is appreciated that various modifications to the invention concepts described herein may be apparent to those of ordinary skill in the art without departing from the scope of the present invention as defined by the appended claims.

The invention claimed is:
1. An assembly that is attachable to an active implantable medical device (AIMD), the assembly comprising:
 a) a feedthrough, comprising:
  i) an electrically conductive ferrule comprising a ferrule sidewall defining a ferrule opening extending to a ferrule body fluid side spaced from a ferrule device side;
  ii) an insulator hermetically sealed to the ferrule in the ferrule opening, the insulator extending to an insulator body fluid side spaced from an insulator device side, wherein, when the ferrule hermetically sealed to the insulator is attached to an opening in a housing of an AIMD, the ferrule body fluid side adjacent to the insulator body fluid side, and the ferrule device side adjacent to the insulator device side reside outside and inside the AIMD, respectively; and
  iii) a first terminal pin hermetically sealed to the insulator in a first via hole by a first braze, and a second terminal pin hermetically sealed to the insulator in a second via hole by a second braze, wherein the first and second terminal pins extend outwardly beyond the insulator device side; and
 b) a polymeric washer positioned on the insulator device side, the polymeric washer comprising at least a washer first opening and a washer second opening through which the respective first and second terminal pins extend, wherein:
  i) the washer first opening comprises a washer first opening inner arcuate portion that contacts the first terminal pin and a washer first opening outer perimeter portion that is spaced from the first terminal pin and that exposes a portion of the first braze hermetically sealing the first terminal pin to the insulator in the first via hole; and ii) the washer second opening comprises a washer second opening inner arcuate portion that contacts the second terminal pin and a washer second opening outer perimeter portion that is spaced from the second terminal pin and that exposes a portion of the second braze hermetically sealing the second terminal pin to the insulator in the second via hole, iii) wherein, in an imaginary configuration having the washer first and second openings superimposed one on top of the other and when measured with respect to their orientations in the polymeric washer, the cumulative arcuate distance of the respective washer first and second opening inner arcuate portions about one of the first and second terminal pins, subtracting overlap, results in a gap between the superimposed washer first and second opening inner arcuate portions that is less than a diameter of either of the first and second terminal pins so that the polymeric washer is prevented from lateral movement with respect to the insulator device side.

2. The assembly of claim 1, wherein the washer first and second inner arcuate portions of the respective washer first and second openings each extend about 90° to about 180° around the respective first and second terminal pins.

3. The assembly of claim 1, wherein the washer first and second outer peripheral portions of the respective washer first and second openings each extend about 90° to about 180° around the respective first and second brazes.

4. The assembly of claim 1, wherein the washer first opening outer peripheral portion extends around at least a portion of the perimeter of the first braze.

5. The assembly of claim 1, wherein the washer first opening inner arcuate portion extends to opposed inner arcuate portion first and third ends and the washer first opening outer peripheral portion extends to opposed outer perimeter portion second and fourth ends, and wherein a first curved edge of the washer first opening meets the first and second ends of the respective inner arcuate and outer perimeter portions at first and second rounded junctions, and wherein a second curved edge of the washer first opening meets the third and fourth ends of the respective inner arcuate and outer perimeter portions at third and fourth rounded junctions.

6. The assembly of claim 1, further comprising a filter capacitor comprising:
a) a dielectric substrate extending to a dielectric substrate first end surface spaced from a dielectric substrate second end surface, wherein the dielectric substrate supports at least one active electrode plate interleaved in a capacitive relationship with at least one ground electrode plate, and wherein the dielectric substrate first end surface is adjacent to the polymeric washer opposite the insulator and ferrule device sides; and
b) at least a first passageway and a second passage extending through the dielectric substrate to the dielectric substrate first and second end surfaces, wherein the first and second terminal pins of the feedthrough extend through the respective first and second passageways and outwardly beyond the dielectric substrate second end surface, and
c) wherein the first terminal pin is electrically connected to one of the active and ground electrode plates in the first passageway by a first electrical connection material, and the second terminal pin is electrically connected to one of the active and ground electrode plates in the second passageway by a second electrical connection material.

7. The assembly of claim 6, wherein the first terminal pin is a first active terminal pin and the first passageway has a capacitor first metallization that is electrically connected to the at least one active electrode plate, and the first electrical connection material connects the first active terminal pin to the capacitor first metallization electrically connected to the at least one active electrode plate in the first passageway, and wherein the second terminal pin is a second active terminal pin and the second passageway has a capacitor second metallization that is electrically connected to the at least one active electrode plate, and the second electrical connection material connects the second active terminal pin to the capacitor second metallization electrically connected to the at least one active electrode plate in the second passageway.

8. The assembly of claim 6, wherein the first terminal pin is an active terminal pin and the first passageway has a capacitor first metallization that is electrically connected to the at least one active electrode plate, and the first electrical connection material connects the first active terminal pin to the capacitor first metallization electrically connected to the at least one active electrode plate in the first passageway, and wherein the second terminal pin is a ground terminal pin and the second passageway has a capacitor second metallization that is electrically connected to the at least one ground electrode plate, and the second electrical connection material connects the second ground terminal pin to the capacitor second metallization electrically connected to the at least one ground electrode plate in the second passageway.

9. The assembly of claim 1, wherein the polymeric washer is selected from silicone, polyurethane, polyester, polyethylene, polypropylene, polyamide, acrylic, polyacrylates, flowable perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), polytetrafluoroethylene, ethylene tetrafluoroethylene, polyetherimide, acetal, polyacetal, polyformaldehyde, phenolic, polysulfide, and combinations thereof.

10. The assembly of claim 9, wherein the polymeric washer includes nanoparticles selected from $Al_2O_3$, BaO, CaO, $CeO_2$, MgO, $ZrO_2$, $SiO_2$, $TiO_2$, $Al_2SiO_{53}$, $BaTiO_3$, $SrTiO_2$, zirconia toughened alumina (ZTA), alumina toughened zirconia (ATZ), yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof.

11. The assembly of claim 10, wherein the nanoparticles range in size from greater than about 100 nanometers (0.1 microns) to about 40,000 nanometers (40 microns).

12. The assembly of claim 10, wherein a nanoparticle loading in the polymeric washer ranges from >0 to about 40%, by weight.

13. A polymeric washer, comprising:
a) a washer first opening comprising a washer first opening inner arcuate portion that is spaced from a washer first opening outer perimeter portion, wherein the washer first opening inner arcuate portion extends to opposed inner arcuate portion first and third ends and the washer first opening outer perimeter portion extends to opposed outer perimeter portion second and fourth ends, and wherein a first curved edge of the washer first opening meets the first and second ends of the respective inner arcuate and outer perimeter portions at first and second junctions, and a second curved edge of the washer first opening meets the third and fourth ends of the respective inner arcuate and outer perimeter portions at third and fourth junctions; and b) a washer second opening comprising a washer second opening inner arcuate portion that is spaced from a washer second opening outer perimeter portion, wherein the washer second opening inner arcuate portion extends to opposed inner arcuate portion fifth and seventh ends and the washer second opening outer perimeter portion extends to opposed outer perimeter portion sixth and eighth ends, and wherein a third curved edge of the washer second opening meets the fifth and sixth ends of the respective inner arcuate and outer perimeter portions at fifth and sixth junctions, and a fourth curved edge of the washer second opening meets the seventh and eighth ends of the respective inner arcuate and outer perimeter portions at seventh and eighth junctions, c) wherein, in an imaginary configuration having the washer first and second openings superimposed one on top of the other and when measured with respect to their orientations in the polymeric washer, the cumulative arcuate distance of the respective washer first and second opening inner arcuate portions, subtracting overlap, results in a gap between the superimposed washer first and second opening inner arcuate portions that is less than a distance between either of the first and third junctions or the fifth and seventh junctions.

14. The polymeric washer of claim 13, selected from silicone, polyurethane, polyester, polyethylene, polypropylene, polyamide, acrylic, polyacrylates, flowable perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), polytetrafluoroethylene, ethylene tetrafluoroethylene, polyetherimide, acetal, polyacetal, polyformaldehyde, phenolic, polysulfide, and combinations thereof.

15. The polymeric washer of claim 13, including nanoparticles selected from $Al_2O_3$, BaO, CaO, $CeO_2$, MgO, $ZrO_2$, $SiO_2$, $TiO_2$, $Al_2SiO_{53}$, $BaTiO_3$, $SrTiO_2$, zirconia toughened alumina (ZTA), alumina toughened zirconia (ATZ), yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof.

16. The polymeric washer of claim 15, wherein the nanoparticles range in size from greater than about 100 nanometers (0.1 microns) to about 40,000 nanometers (40 microns).

17. The polymeric washer of claim 15, wherein a nanoparticle loading in the polymeric washer ranges from >0 to about 40%, by weight.

18. The polymeric washer of claim 13, wherein the washer first and second inner arcuate portions of the respective washer first and second openings each extend for about 90° to about 180° to the first and third junctions for the washer first opening inner arcuate portion and to the fifth and seventh junctions for the washer second opening inner arcuate portion, and wherein the washer first and second outer peripheral portions of the respective washer first and second openings each extend for about 90° to about 180° to the second and fourth junctions for the washer first opening outer perimeter portion and to the sixth and eighth junctions for the washer second opening outer perimeter portion.

19. An electromagnetic interference (EMI) filtered hermetic feedthrough terminal for an active implantable medical device (AIMD), the EMI filtered hermetic feedthrough terminal comprising:

a) a metallic ferrule configured to be mounted into an opening of an AIMD housing including an outer perimeter and an inner perimeter, wherein after installation into the AIMD housing, the metallic ferrule has a device side oriented to the inside of the AIMD housing and a body fluid side oriented to the outside of the AIMD housing;

b) an insulator mounted to the ferrule inner perimeter, the insulator thereby also having a device side and a body fluid side;

c) a hermetic sealing material between the insulator and the ferrule;

d) a plurality of feedthrough terminal pins mounted within and extending through a respective one of a plurality of insulator passageways;

e) a hermetic sealing material between each of the plurality of terminal pins and a respective one of the plurality of insulator passageways;

f) a self-centering polymeric insulating washer with a plurality of non-circular irregular openings configured to slip down over each of the plurality of terminal pins, wherein the polymeric insulating washer is seated against one or both of the insulator device side and the ferrule device side;

g) the self-centering polymeric insulating washer non-circular irregular openings each having a defined asymmetrical shape to contact each terminal pin in selected clocked positions thereby constraining movement of the self-centering polymeric insulating washer in a planar or x-y direction with respect to the ferrule device side; and h) an EMI feedthrough filter capacitor or an EMI filter circuit board having a plurality of circular through passageways or vias for passage of the plurality of terminal pins, wherein the EMI feedthrough filter capacitor or the EMI filter circuit board is mounted directly against the self-centering polymeric insulating washer opposite the one or both of the insulator device side and the ferrule device side.

20. An assembly that is attachable to an active implantable medical device (AIMD), the assembly comprising:

a) a feedthrough, comprising:

i) an electrically conductive ferrule comprising a ferrule sidewall defining a ferrule opening extending to a ferrule body fluid side spaced from a ferrule device side;

ii) an insulator hermetically sealed to the ferrule in the ferrule opening, the insulator extending to an insulator body fluid side spaced from an insulator device side, wherein, when the ferrule hermetically sealed to the insulator is attached to an opening in a housing of an AIMD, the ferrule body fluid side adjacent to the insulator body fluid side, and the ferrule device side adjacent to the insulator device side reside outside and inside the AIMD, respectively; and iii) at least a first terminal pin hermetically sealed to the insulator in a first via hole by a first braze, wherein the first terminal pin extends outwardly beyond the insulator device side; and b) a polymeric washer positioned on the insulator device side, the polymeric washer having at least a first opening comprising at least two spaced-apart washer first opening inner arcuate portions that extend inwardly from a washer first opening outer perimeter comprising at least two spaced-apart washer first opening outer perimeter portions, wherein the at least two spaced-apart washer first opening inner arcuate portions are in contact with the first terminal pin so that the polymeric washer is prevented from any lateral movement with respect to the insulator device side, and wherein the at least two washer first opening outer perimeter portions are spaced from the first terminal pin to expose at least two portions of the first braze hermetically sealing the first terminal pin to the insulator in the first via hole.

21. The assembly of claim 20, wherein the washer first opening comprises four spaced-apart washer first opening inner arcuate portions that extend inwardly from the washer first opening outer perimeter comprising at least four spaced-apart washer first opening outer perimeter portions, wherein the at least four spaced-apart washer opening first inner arcuate portions are in contact with the first terminal pin so that the polymeric washer is prevented from lateral movement with respect to the insulator device side, and wherein the at least four spaced-apart washer first opening outer perimeter portions are spaced from the first terminal pin to expose at least four portions of the first braze hermetically sealing the first terminal pin to the insulator in the first via hole.

22. The assembly of claim 20, further comprising:
a) at least a second terminal pin hermetically sealed to the insulator in a second via hole by a second braze, wherein the second terminal pin extends outwardly beyond the insulator device side; and
b) the polymeric washer having a second opening comprising at least two spaced-apart washer second opening inner arcuate portions that extend inwardly from a washer second opening outer perimeter comprising at least two spaced-apart washer second opening outer perimeter portions, wherein the at least two spaced-apart washer second opening inner arcuate portions are in contact with the second terminal pin, and wherein the at least two washer second opening outer perimeter portions are spaced from the second terminal pin to expose at least two portions of the second braze hermetically sealing the second terminal pin to the insulator in the second via hole.

23. The assembly of claim 22, wherein at least one of the at least two spaced-apart washer first opening inner arcuate portions and the at least two spaced-apart washer second opening inner arcuate portions are diametrically opposed to each other.

* * * * *